US009650406B2

(12) United States Patent
Zhou et al.

(10) Patent No.: US 9,650,406 B2
(45) Date of Patent: May 16, 2017

(54) REVERSIBLE TERMINATOR MOLECULES AND METHODS OF THEIR USE

(71) Applicant: CENTRILLION TECHNOLOGY HOLDINGS CORPORATION, Palo Alto, CA (US)

(72) Inventors: Wei Zhou, Palo Alto, CA (US); Glenn McGall, Palo Alto, CA (US); Moti Jain, Palo Alto, CA (US); Rui Mei, Palo Alto, CA (US)

(73) Assignee: CENTRILLION TECHNOLOGY HOLDINGS CORPORATION, Palo Alto, CA (US)

(*) Notice: Subject to any disclaimer, the term of this patent is extended or adjusted under 35 U.S.C. 154(b) by 551 days.

(21) Appl. No.: 13/952,377

(22) Filed: Jul. 26, 2013

(65) Prior Publication Data
US 2014/0242579 A1    Aug. 28, 2014

Related U.S. Application Data

(60) Provisional application No. 61/770,525, filed on Feb. 28, 2013.

(51) Int. Cl.
*C07H 19/00*    (2006.01)
*C07H 21/02*    (2006.01)
(Continued)

(52) U.S. Cl.
CPC ............. *C07H 19/10* (2013.01); *C07H 19/20* (2013.01); *C07H 21/00* (2013.01)

(58) Field of Classification Search
CPC ................................ C07H 19/10; C07H 21/00
(Continued)

(56) References Cited

U.S. PATENT DOCUMENTS

| 5,302,509 A | 4/1994 | Cheeseman |
| 5,547,839 A | 8/1996 | Dower et al. |

(Continued)

FOREIGN PATENT DOCUMENTS

| WO | WO 93/21340 A1 | 10/1993 |
| WO | WO 2005/024010 A1 | 3/2005 |

(Continued)

OTHER PUBLICATIONS

Sobkowski et al. Tetrahedron: Asymmetry 18 (2007) 2336-2348.*
(Continued)

*Primary Examiner* — Jezia Riley
(74) *Attorney, Agent, or Firm* — Birch, Stewart, Kolasch & Birch, LLP

(57) ABSTRACT

The present invention relates generally to methods of sequencing of polynucleotides and compounds, compositions and kits useful for sequencing of polynucleotides. The chemical compounds include nucleotide and nucleoside analogs which possess a blocking group covalently attached to the 3' hydroxyl of the sugar moiety. The blocking group may optionally be additionally covalently attached to a linker and/or detectable label. The nucleotide analogs may be ribonucleotide or deoxyribonucleotide analogs. Methods include incorporation of the reversible terminator molecules into growing polynucleotide strands by polymerase enzymes, such as in single base sequencing methodologies utilizing sequential reversible termination techniques.

51 Claims, 3 Drawing Sheets

(51) Int. Cl.
  C07H 19/04    (2006.01)
  C07H 19/10    (2006.01)
  C07H 21/00    (2006.01)
  C07H 19/20    (2006.01)
  C12Q 1/68     (2006.01)

(58) Field of Classification Search
  USPC .................. 536/4.1, 23.1, 26.6; 435/6.12
  See application file for complete search history.

(56) References Cited

U.S. PATENT DOCUMENTS

| | | | |
|---|---|---|---|
| 5,580,731 A * | 12/1996 | Chang | C07H 21/00 435/5 |
| 5,763,594 A | 6/1998 | Hiatt et al. | |
| 5,808,045 A | 9/1998 | Hiatt et al. | |
| 5,872,244 A | 2/1999 | Hiatt et al. | |
| 6,214,987 B1 | 4/2001 | Hiatt et al. | |
| 6,232,465 B1 | 5/2001 | Hiatt et al. | |
| 6,632,655 B1 * | 10/2003 | Mehta | B01L 3/5027 435/287.2 |
| 7,566,537 B2 | 7/2009 | Balasubramanian et al. | |
| 7,592,435 B2 | 9/2009 | Milton et al. | |
| 8,399,188 B2 | 3/2013 | Zhao et al. | |
| 2003/0215862 A1 | 11/2003 | Parce et al. | |
| 2005/0037991 A1 * | 2/2005 | Bodepudi | C07H 19/00 514/47 |
| 2011/0045489 A1 | 2/2011 | Gardner et al. | |
| 2013/0085073 A1 * | 4/2013 | Meuleman | C12Q 1/6874 506/2 |

FOREIGN PATENT DOCUMENTS

WO    WO 2006/120433 A1    11/2006
WO    WO 2007/075967 A2    7/2007

OTHER PUBLICATIONS

Vaillancourt et al. e-EROS Encyclopedia of Reagents for Organic Synthesis (2001), 1-2.*
Mikkola et al. J. Chem. Soc., Perkin Trans. 2, 1999, 1619-1625.*
Ansorge, "Next-generation DNA sequencing techniques", New Biotechnology, vol. 25, No. 4, Apr. 2009, pp. 195-203.
Berglund et al., "Next-generation sequencing technologies and applications for human genetic history and forensics", Investigative Genetics, vol. 2, No. 23, 2011, 15 pages.
Canard et al., "DNA polymerase fluorescent substrates with reversible 3'-tags", Gene, vol. 148, 1994, pp. 1-6.
Fuller et al., "The challenges of sequencing by synthesis", Nature Biotechnology, vol. 27, No. 11, Nov. 2009, pp. 1013-1023 (13 pages provided).
Gardner et al., "Acyclic and dideoxy terminator preferences denote divergent sugar recognition by archaeon and Taq DNA polymerases", Nucleic Acids Research, vol. 30, No. 2, 2002, pp. 605-613.
Guo et al., "Four-color DNA sequencing with 3'-0-modified nucleotide reversible terminators and chemically cleavable fluorescent dideoxynucleotides", PNAS, vol. 105, No. 27., Jul. 8, 2008, pp. 9145-9150.
Ju et al., "Four-color DNA sequencing by synthesis using cleavable fluorescent nucleotide reversible terminators", PNAS, vol. 103, No. 52, Dec. 26, 2006, pp. 19635-19640.
Korlach et al., "Long, Processive Enzymatic DNA Synthesis Using 100% Dye-Labeled Terminal Phosphate-Linked Nucleotides", Nucleosides, Nucleotides and Nucleic Acids, vol. 27, No. 9, 2008, pp. 1072-1083.
Marras, "Selection of Fluorophore and Quencher Pairs for Flourescent Nucleic Acid Hybridization Probes", Methods in Molecular Biology, vol. 335, 2006, pp. 3-16.
Metzker et al., "Termination of DNA synthesis by novel 3'-modified-deoxyribonucleoside 5'-triphosphates", Nucleic Acids Research, vol. 22, No. 20, 1994, pp. 4259-4267.
Metzker, "Sequencing technologies—the next generation", Nature Reviews/Genetics, Jan. 2010 (published online Dec. 8, 2009), vol. 11, pp. 31-46.
Niedringhaus et al., "Landscape of Next-Generation Sequencing Technologies", Analytical Chemistry, vol. 83, May 25, 2011, pp. 4327-4341.
Ruparel et al., "Design and synthesis of a 3'-0-allyl photocleavable fluorescent nucleotide as a reversible terminator for DNA sequencing by synthesis", PNAS, vol. 102, No. 17, Apr. 26, 2005, pp. 5932-5937.
Sood et al., "Terminal Phosphate-Labeled Nucleotides with Improved Substrate Properties for Homogeneous Nucleic Acid Assays", J. Am. Chem. Soc., vol. 127, No. 8, 2005 (published online Feb. 3, 2005), pp. 2394-2395 and S1-S15.
Southworth et al., "Cloning of thermostable DNA polymerases from hyperthermophilic marine Archaea with emphasis on *Thermococcus* sp. 9° N-7 and mutations affecting 3'-5' exonuclease activity", Proc. Natl. Acad. Sci. USA, vol. 93, May 1996, pp. 5281-5285.
Tabor et al., "A single residue in DNA polymerases of the *Escherichia coli* DNA polymerase I family is critical for distinguishing between deoxy-and dideoxyribonucleotides", Proc. Natl. Acad. Sci. USA, vol. 92, Jul. 1995, pp. 6339-6343.
Thompson et al., "The properties and applications of single-molecule DNA sequencing", Genome Biology, vol. 12, No. 217, 2011, 10 pages.

* cited by examiner

REVERSIBLE TERMINATOR MOLECULES AND METHODS OF THEIR USE

CROSS-REFERENCE TO RELATED APPLICATIONS

The present application claims priority of Provisional U.S. Patent Application Ser. No. 61/770,525, filed on Feb. 28, 2013.

FIELD OF THE INVENTION

The field relates generally to methods of determining the sequence of polynucleotides and compounds, compositions and kits useful in determining the sequence of polynucleotides, genotyping, and controlled nucleic acid synthesis.

BACKGROUND OF THE INVENTION

The modern era of automated, high-throughput nucleic acid sequencing began with large-scale application of the Sanger sequencing method for the The Human Genome Project. The Sanger method used chain-terminating inhibitors, one for each nucleotide—C, T, A, and G—each of which contained a detectable label and which, when incorporated into a nucleotide strand, inhibited further progress of the polymerase enzyme used in the method. (See, Sanger et al., "DNA sequencing with chain-terminating inhibitors," *Proc. Natl. Acad. Sci. USA*, 74:5463-5467, 1977). These prematurely terminated sequences, which were complementary to the target sequence, were then separated and detected by gel electrophoresis. This method is still used today in basic and applied scientific research. The Sanger method has also been automated, providing a technology that some refer to as the "first generation" of polynucleotide sequencing. (Metzker, Michael A., "Sequencing technologies—the next generation," *Nature Rev. Gen.*, 11:31-46, 2010.) However, science has marched on since disclosure of the Sanger method and today, more than three decades later, additional strategies available for determining the sequence of a polynucleotide have been developed.

The new methods, commonly referred to as Next Generation Sequencing (NGS) or "massively parallel" methods, coupled with improvements in methods involving the polymerase chain reaction (PCR) for amplifying target polynucleotides, have catapulted the study of nucleotide sequences into increasingly more diverse areas of application. Consequently, the market for sequencing has been estimated to be over one billion USD in 2011, and is expected to double by 2016. (See, "Research and Markets: Next Generation Sequencing: Market Size, Segmentation, Growth and Trends by Provider 2011," *Business Wire*, Nov. 30, 2011).

Whereas the Human Genome Project cost over three billion US dollars and required nearly thirteen years to complete, today a whole genome may be sequenced using NGS technology in 24 hours at a fraction of the cost. Over the first decade of the $21^{st}$ century, technology innovation in NGS progressed towards a long-sought "$1000 genome." (See, Wolinsky, Howard, "The thousand-dollar genome. Genetic brinkmanship or personalized medicine?" *EMBO Rep.*, 8(10):900-903, 2007). In 2007, the genomic sequence of James D. Watson was obtained using NGS technologies at a cost of approximately one million US dollars. Dr. Watson's genetic sequence was published in 2008. (See, Wheeler et al., "The complete genome of an individual by massively parallel DNA sequencing," *Nature* 452(7189): 872-876, 2008). Later in 2007, an individual could purportedly obtain their genomic sequence for the price of 350,000 US dollars. (See, Amy Harmon, "Gene map becomes a luxury item," *New York Times*, Mar. 4, 2008). The $50,000 human genome was first offered around 2010. (See, Dewey et al., "Phased Whole-Genome Genetic Risk in a Family Quartet Using a Major Allele Reference Sequence," *PLoS Genetics* 7(9): e1002280, 2011). In 2012, the ability to sequence an entire human genome within one day for a cost of approximately $1,000 was advertised. (See, Defrancesco, L., "Life Technologies promises $1,000 genome," *Nature Biotechnology* 30(2): 126, 2012). Instead of striving for obtaining the sequence information for a single human genome, scientists are now striving towards obtaining the sequence information of 1,000 genomes.

These new high throughput NGS (HT-NGS) methods may potentially allow scientists to obtain the sequence of genes more quickly and at less cost. (See, Smith, Caitlin, "Whole Genome Sequencing Technologies Enhance Speed and Throughput," *Biocompare*, Apr. 25, 2013 and Mardis, E R, "A decade's perspective on DNA sequencing technology," *Nature*, 470(7333):198-203, 2011). However, it is recognized that the efficiency of HT-NGS is sometimes obtained at the cost of accuracy and fidelity. Error rates continue to be a concern in employing these methods, especially in the clinical fields. Thus, maintaining low cost profiles while increasing sensitivity are all matters that continue to receive much attention and continued innovation. Longer reads, i.e. longer continuous sequence determinations on longer strands of nucleic acid, offers higher fidelity, but are technically more difficult to achieve and sometimes require more time and resources to obtain. Shorter reads, i.e. obtaining the sequence information from a shorter nucleotide, are easier and can be performed in massively parallel systems, offering higher fidelity than might otherwise be expected, but may be less useful in a clinical setting.

The issue of accuracy in NGS may be addressed by ensuring that sequences are not determined in a low fidelity environment. For instance, in the context of sequencing by synthesis (SBS), polymerase enzymes are used to determine the identity of the next base needed in the growing strand and to catalyze its incorporation. Non-native nucleotides are often utilized in SBS methodologies to arrest the progression of strand synthesis, allowing determination of the identity of the incorporated base. However, the fidelity of polymerase enzymes drops when tasked with incorporating non-native nucleotides into the growing DNA strand. There is a long felt need in the field of HT-NGS to increase fidelity in SBS and to develop nucleotides for use in sequential reversible termination which meet all assay requirements, providing efficient, quantitative termination and reversibility, acceptable accuracy, avoids harsh chemical conditions, and does not slow down polymerase activity. The present application provides such non-native nucleotides useful in SBS methodologies.

SUMMARY OF THE INVENTION

The chemical compounds disclosed herein include reversible terminator molecules, i.e. nucleoside and nucleotide analogs which possess a variable phosphodiester blocking group covalently attached to the 3' hydroxyl of the nucleotide sugar moiety. The covalent linkage to the 3' hydroxyl is reversible, meaning the variable phosphodiester group may be removed by chemical and/or enzymatic processes. The nucleotide/nucleoside analog may optionally include a linker and one or more detectable labels. The one or more detectable labels may optionally be quenchable. The nucleotide analogs may be ribonucleotide or deoxyribonucleotide molecules and analogs, and derivatives thereof. Presence of the covalently bound variable group is designed to impede progress of polymerase enzymes used in methods of enzyme-based polynucleotide synthesis.

More specifically, the disclosed compounds are represented in Formulas I through VI, as follows:

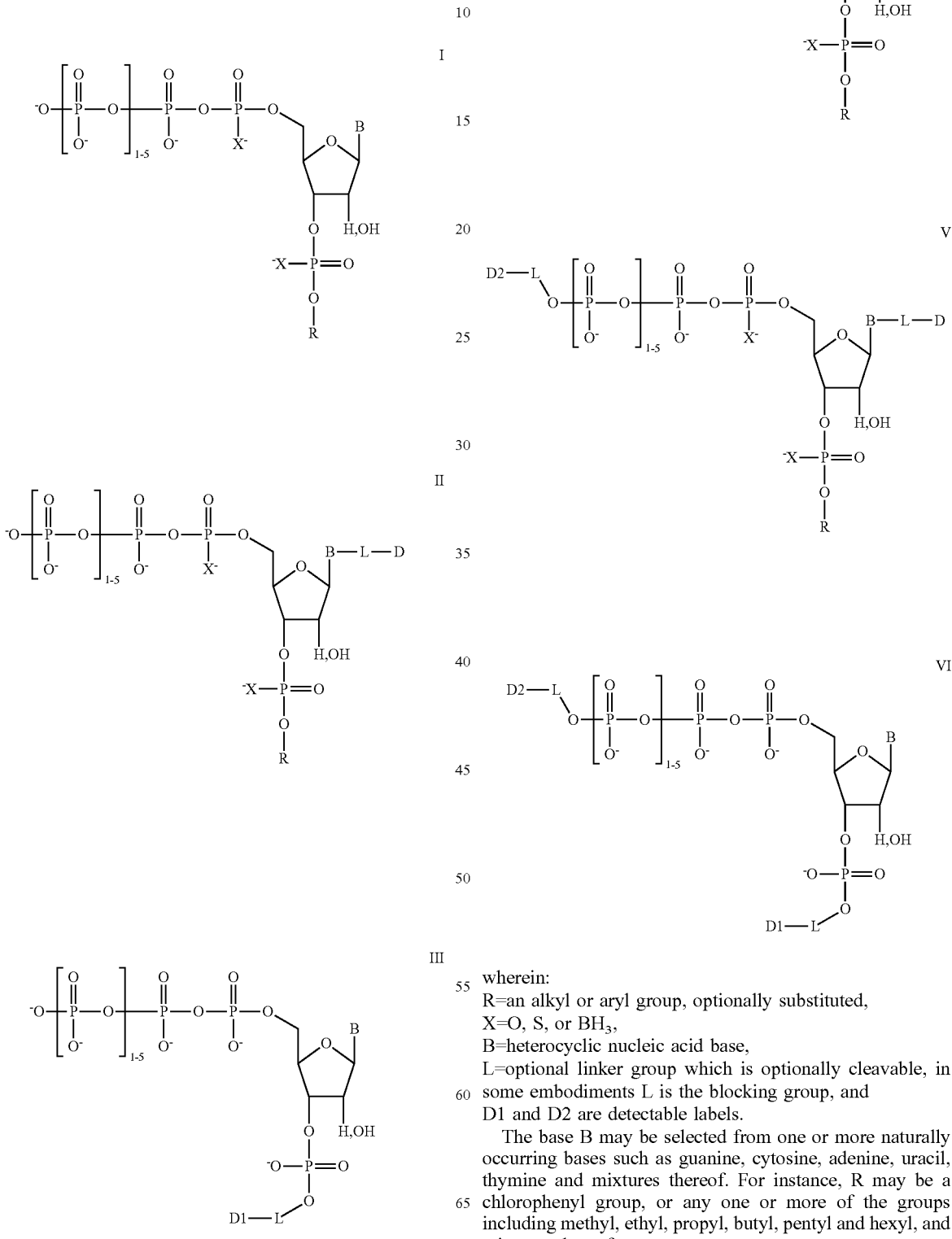

wherein:
R=an alkyl or aryl group, optionally substituted,
X=O, S, or $BH_3$,
B=heterocyclic nucleic acid base,
L=optional linker group which is optionally cleavable, in some embodiments L is the blocking group, and
D1 and D2 are detectable labels.

The base B may be selected from one or more naturally occurring bases such as guanine, cytosine, adenine, uracil, thymine and mixtures thereof. For instance, R may be a chlorophenyl group, or any one or more of the groups including methyl, ethyl, propyl, butyl, pentyl and hexyl, and mixtures thereof.

The linker L contemplated herein has the structure depicted in Scheme I:

Scheme I

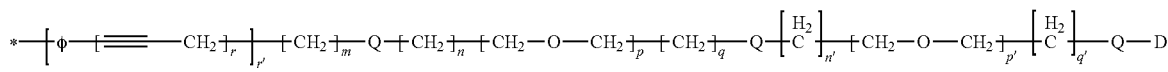

wherein:
m is an integer from 0 to 9,
r and r' are individually either 0 or 1
n and n' are individually either 1 or 2,
p and p' are individually integers from 0 to 18,
q and q' are individually either 1 or 2,
D is a detectable label,
Φ is a cyclic alkane or alkene, an aromatic, heterocyclic or fused ring structure, and
Q is an optional connecting group.

More particularly, for instance, the linker may be any one or more of the following:
—(CH$_2$)$_6$—NHC(O)(CH$_2$)$_n$—NHC(O)—,
—CH$_2$(CH$_2$OCH$_2$)$_3$CH$_2$—NHC(O)—(CH$_2$)$_n$—NHC(O)—,
CH$_2$CH(CH$_2$CH$_2$OH)(OCH$_2$CH$_2$)$_n$—NHC(O)—(CH$_2$)$_n$—NHC(O)—, As an example, the variable group Q, from Scheme I, above, may be any one or more of the following:

—O—, —S—S—,

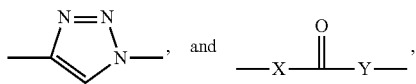

wherein X and Y may be defined as O, S, NH$_2$, CH$_2$, or, for instance, the group

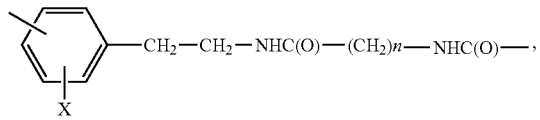

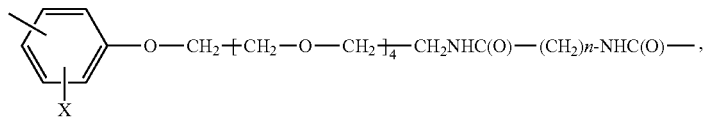

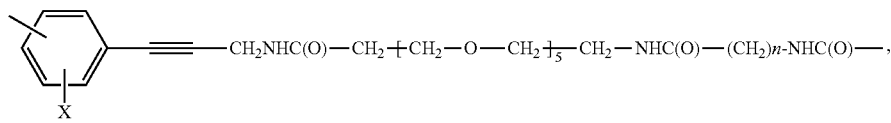

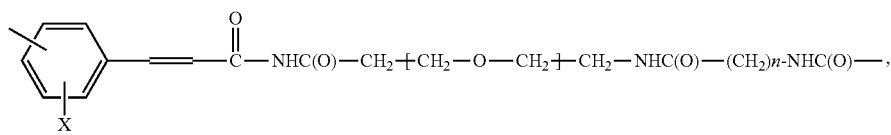

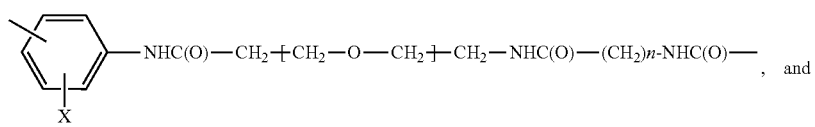

, and

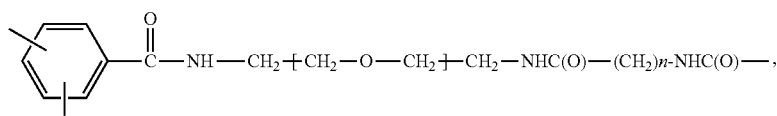

wherein X is an optional substituent.

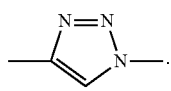

For instance, X may be a halogen, such as any one or more of fluorine, chlorine, bromine, iodine, astatine and mixtures thereof. Further, the label D may be one or more different fluorescent detectable labels, or mixtures thereof. That is, each different reversible terminator nucleotide may be attached to a different label, thereby allowing individual detection of each different type of reversible terminator. More particularly, the nucleotide bases A, C, T, and G, may be substituted for "B" in the Formulas described above, and for instance each such reversible terminator may individually be covalently attached to a different detectable fluorescent label, allowing four-color detection of the reversible terminators disclosed herein.

Presently disclosed are methods of using these compounds and kits containing these compounds for performing such methods. The methods disclosed include a method of sequencing a polynucleotide by performing a polymerization reaction in a reaction system comprising a target polynucleotide to be sequenced, one or more polynucleotide primers which hybridize with the target polynucleotide to be sequenced, a catalytic amount of a polymerase enzyme and the compound of claim 1.

Compounds disclosed herein also include nucleosides comprising a sugar moiety, wherein the sugar moiety has covalently bound thereto at the 3' hydroxyl group a phosphate moiety and a removable blocking group, wherein the blocking group is an alkyl or aryl group, such as the reversible terminator groups described above. The blocking group may comprise a substituted alkyl or aryl group and the nucleoside may have covalently attached to its 5' hydroxyl group one or more phosphate groups, maybe even, for instance, 3, 4 or even 5 phosphate groups. Preferably, the blocking group is removable by incubation with one or more enzymes, i.e. the reversible terminator compounds presently disclosed are enzymatically removable, though they may be covalently attached to the nucleotide. The enzymes used to remove the reversible terminator, in sequential reversible termination reactions for sequencing nucleotides, may include, for instance, phosphodiesterases and/or phospholipases, and/or mixtures thereof. The blocking group will typically further include a linker moiety, as described above, and optionally a label.

In one embodiment, contemplated herein, the linker is enzymatically cleavable. Of course, the linker must be synthesized to be long enough to allow enzymatic removal of the linker, if so desired. That is, the linker must not create steric hindrance precluding removal by an enzyme, such as a phosphodiesterase or phospholipase.

In another embodiment, the phosphate moiety covalently attached to the 3' hydroxyl group of the disclosed reversible terminators includes at least one sulfur atom or $BH_3$ group substituted for one of the non-bonding phosphate oxygen atoms. Further contemplated are reversible terminators wherein the 2' group on the sugar moiety has covalently attached thereto a hydroxyl group.

DETAILED DESCRIPTION OF THE INVENTION

Figure 1:
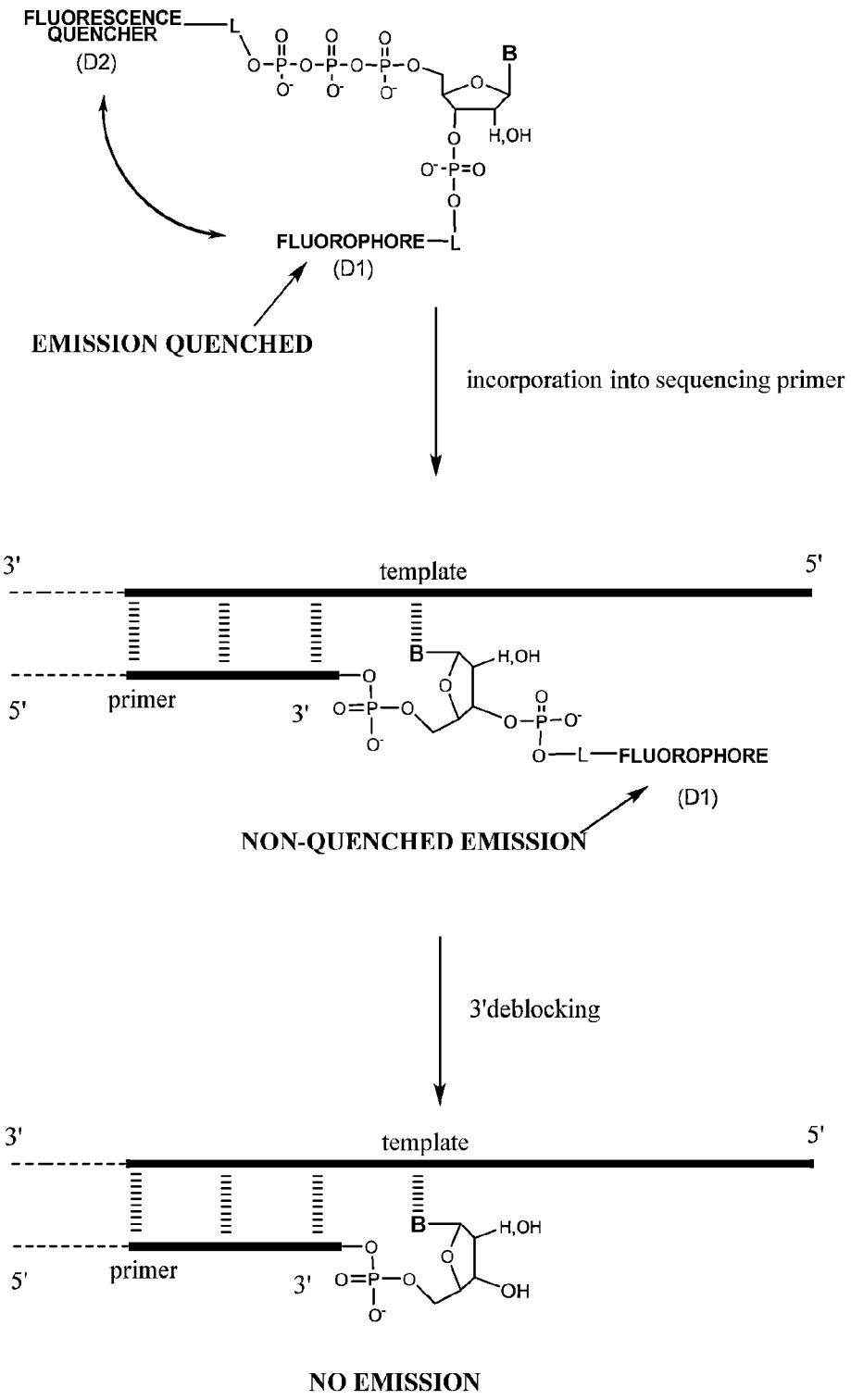
FIG. 1: Depiction showing mechanism of detection of incorporation of reversible terminator molecules using an emitter-quencher method.

Nucleotide sequence information is used in a myriad different ways by scientists, researchers and individuals to improve their lives either through clinical means or by material means, e.g. improving crop production, creating better fuel, making a better vaccine, creating more effective pharmaceuticals, preventing disease, or preventing an outbreak of a dangerous pathogen. (See, Ansorge, Wilhelm J., "Next-generation DNA sequencing techniques," *New Biotech.*, 25(4):195-203, 2009).

Scientists working in academic settings and industry in many fields, including genetics and biology, use sequencing methods to associate mutations in genomes with diseases and phenotypes, predispositions to diseases, diagnosis of disease, prognosis of disease, to explain evolutionary biology, to determine whether a particular course of medication is appropriate for a subject suffering from one or more disease, i.e. which patients will respond best to specific drugs, i.e. personalized medicine, to convict criminals in forensics fields, to predict disease and genetic heredity in pre-natal applications, to study cancer and tumor biology, to identify contagion such as bacteria and viruses, and so on. All of these fields require access to technologies that allow scientists to rapidly, efficiently and accurately obtain sequence information from patients, organisms, and/or infectious agents. (See, for instance, Na et al., "AnsNGS: An Annotation System to Sequence Variations of Next Generation Sequencing Data for Disease-Related Phenotypes," *Healthc. Inform. Res.*, 19(1):50-5, 2013; Mwenifumbo et al., "Cancer genome-sequencing study design," *Nature Reviews Genetics*, 14:321-332, 2013; Didelot et al., "Transforming clinical microbiology with bacterial genome sequencing," *Nature Reviews Genetics*, 13(9):601-612, 2012; Morozova et al., "Applications of next-generation sequencing technologies in functional genomics," *Genomics*, 92(5):255-264, 2008; and Marquerat et al., "Next-generation sequencing: applications beyond genomes," *Biochem. Soc. Trans.*, 36(Pt. 5):1091-1096, 2008).

In some fields of study, determination of the DNA sequence of an entire genome is sought. With the age of NGS, whole genomes of such diverse organisms as wheat, cat, tomato, rhinoceros, gorilla, corn, zebrafish, *bacillus anthracis*, red flour beetle, and even platypus have been determined. In each instance, the whole genome provided researchers, scientists and the general public with insights into the organism's life. (See, for instance, Perkel, Jeffrey M., "Next Generation Sequencing 2013: Looking into Genomes," *Biocompare*, Jan. 29, 2013).

In other fields, genetic sequences of only certain species of RNA and DNA are sufficient. Often scientists merely seek the identity of the nucleotide sequence of transcribed genes, commonly referred to as the transcriptome. (See, for instance, Stiles et al., "Gene expression analysis reveals marked differences in the transcriptome of infantile hemangioma endothelial cells compared to normal dermal microvascular endothelial cells," *Vascular Cell*, 5:6, 2103). Some companies focus on merely providing the sequence of specific mutations in samples by use of such legacy technology as the GENECHIP®, provided by Affymetrix, Inc. Others seek to identify the sequence of only chloroplasts, or mitochondria, or microRNA species, etc.

Furthermore, advances in NGS have made gene sequencing available to an increasingly diverse user base and allowed broader application. Further accelerating the utilization of this technology are advances in instrumentation. Instrumentation for (HT) NGS is even available as in a bench top form. (See, Loman et al., "Performance comparison of benchtop high-throughput sequencing platforms," *Nature Biotech.*, 30(5):434-439, 2012). For instance, Intelligent Biosystems (a Qiagen company in Waltham, Mass., US) offers a sequencing-by-synthesis (SBS) instrument that fits on the bench top and provides a human whole genome sequence (WGS) in a matter of hours for the approximate cost of five thousand US dollars. Other companies also offer bench top solutions to the scientist seeking high-throughput nucleotide sequencing. Loman et al. compare three bench top sequencing platforms by testing their ability to sequence the genome of *E. coli* isolate 0104:H4. One instrument tested in the study employs emulsion PCR technology (also referred to as "molecular BEAMing"). (See, Dressman et al., "Transforming single DNA molecules into fluorescent magnetic particles for detection and enumeration of genetic variants," *Proc. Nat. Acad. Sci. USA*, 100(15):8817-8822, 2003; and Williams et al., "Amplification of complex gene libraries by emulsion PCR," *Nature Methods*, 3(7):545-550, 2006).

The speed and low cost of NGS is sometimes obtained at the sacrifice of accuracy and depth of sequence information. To obtain sequences in a fast and accurate way requires long reads and numerous iterations of determining the sequence of the same gene to be sure it is correct. Thus, as the term "massively parallel" implies, in HT-NGS the sequence of one polynucleotide is determined many times in parallel and cross-checked against all reads to obtain a result of high confidence. This is commonly referred to as "coverage" and may be as low as 30× or 40× in some applications, i.e. the same nucleotide sequenced 30 times or 40 times, to as high as 180× or 200× in other applications that require teasing out specific point mutations in, for instance, cancer tumors. Higher coverage rates, or "deep reads," are more expensive and require more time. Thus, NGS technology, while offering great hope and expectations, carries with it a degree of uncertainty and issues that can cloud interpretation of the data and application in fields that require high efficiency as well as high accuracy. (See, for instance, Fuller et al., "The challenges of sequencing by synthesis," *Nat. Biotech.*, 27(11):1013-1023, 2009). Additional solutions are needed to continue to mature this technology so that it may continue to be applied in more fields.

There have been attempts to synthesize useful reversible terminator nucleotide/nucleoside analogs useful in sequential reversible termination reactions, such as by including modifications at the 2' and/or 4' oxygen. However, many of these attempts have been unsuccessful or not adequately tested. Further, the ideal location for a modification would be at the 3' position of the nucleotide/nucleoside. Previous reported attempts to create such analogs that are functional and useful have been stymied due to the sensitivity of polymerase enzymes of modifications at that position. (See, for instance, U.S. Pat. No. 8,399,188, at page 4; Metzker et al., "Termination of DNA synthesis by novel 3'-modified deoxyribonucleoside triphosphates," *Nucleic Acids Res.* 22:4259-4267 (1994); Canard et al., "DNA polymerase fluorescent substrates with reversible 3'-tags," *Gene*, 148, 1-6 (1994); Ju et al., "Four-color DNA sequencing by synthesis using cleavable fluorescent nucleotide reversible terminators," *Proc. Natl. Acad. Sci. USA*, 103:19635-19640 (2006); Guo et al., "Four-color DNA sequencing with 3'-O-modified nucleotide reversible terminators and chemically cleavable fluorescent dideoxynucleotides," *Proc. Natl. Acad. Sci. USA* 105:9145-9150 (2008)).

Therefore, there is a need to develop nucleotide analogs that work well with polymerase enzymes and are able to terminate strand growth upon incorporation into the growing strand. A pause in polymerase activity during strand elongation caused by a reversible terminator nucleotide analog allows accurate determination of the identity of the incorporated nucleic acid. Ability to continue strand synthesis after this accurate determination is made would be ideal, through subsequent modification of the reversible terminator nucleotide analog that allows the polymerase enzyme to continue to the next position on the growing DNA strand. The process of arresting DNA polymerization followed by removal of the blocking group on the incorporated non-native nucleotide is referred to herein as sequential reversible termination. Another requirement of sequential reversible termination is that the non-native nucleotide analog must be easily removed without damaging the growing DNA strand or the polymerase, i.e. termination must be reversible under mild reaction conditions. Previous attempts to design such analogs mainly utilize harsh chemical conditions to remove the non-native nucleotide analog.

After much effort in experimentation, Applicants have fortuitously found non-native nucleotide analogs that meet these stringent criteria. These analogs possess a reversible covalent modification on the oxygen atom of the 3' phosphate group of the nucleotide. As explained in further detail below, these analogs are fully reversible under mild conditions. The covalent modification of the nucleotide is removed by enzymatic means, providing a high degree of specificity and sufficiently gentle conditions to avoid negatively impacting the processivity or fidelity of the polymerase enzyme. These analogs are most useful in the context of SBS, but may be employed elsewhere as may be apparent to one of skill in the art.

Sequencing Targets and Preparation

Genetic material useful as targets for the present sequencing methods and compositions include, but are not limited to, DNA and RNA. It is known that there many different types of RNA and DNA, all of which have been and continue to be the subject of great study and experimentation. Targets of DNA may include, but are not limited to, genomic DNA (gDNA), chromosomal DNA, mitochondrial DNA (mtDNA), plasmid DNA, ancient DNA (aDNA), all forms of DNA including A-DNA, B-DNA, and Z-DNA, branched DNA, and non-coding DNA. Preferred forms of DNA are those which can optionally be amplified and those that possess a linear sequence of nucleosides. Forms of RNA that may be sequenced using the present methods and compositions include, but are not limited to, messenger RNA (mRNA), ribosomal RNA (rRNA), microRNA, small RNA, snRNA and non-coding RNA. (See, Limbach et al., "Summary: The modified nucleosides of RNA," *Nuc. Acids Res.*, 22(12):2183-2196, 1994).

Nucleotides include, but are not limited to the native nucleotides G, C, A, T and U, as well as rare forms, such as, Inosine, Xanthosine, 7-methylguanosine, dihydrouridine, 5-methylcytosine, and pseudouridine, including methylated forms of G, A, T, and C, and the like. (See, for instance, Korlach et al., "Going beyond five bases in DNA sequencing," *Curr. Op. Struct. Biol.*, 22(3):251-261, 2012, and U.S. Pat. No. 5,646,269, especially columns 17-19). Nucleosides may also be non-naturally occurring molecules, such as those comprising 7-deazapurine, pyrazolo[3,4-d]pyrimidine, propynyl-dN, or other analogs or derivatives as disclosed herein or are well known in the art. Exemplary nucleosides include ribonucleosides, deoxyribonucleosides, dideoxyribonucleosides, carbocyclic nucleosides, and the like.

Samples

Generally, any sample containing genetic material possessing a sequence of nucleotides may be amenable to the present methods and compositions. Samples may be obtained from any of the kingdoms of eukaryotes, prokaryotes and archaea. For example, samples containing genetic material whose sequence may be determined using the present methods and compositions include those obtained from, for instance, bacteria, bacteriophage, virus, transposons, mammals, plants, fish, insects, etc.

Samples may be human in origin and may be obtained from any human tissue containing genetic material. Generally, the samples may be fluid samples, such as, but not limited to normal and pathologic bodily fluids and aspirates of those fluids. Bodily fluids include, but are not limited to, whole blood, bone marrow aspirate, synovial fluid, cerebrospinal fluid, saliva, sweat, tears, semen, sputum, mucus, menstrual blood, breast milk, urine, lymphatic fluid, amniotic fluid, placental fluid and effusions such as cardiac effusion, joint effusion, pleural effusion, and peritoneal cavity effusion (ascites). Rinses can be obtained from numerous organs, body cavities, passage ways, ducts and glands, such as, but not limited to lungs (bronchial lavage), stomach (gastric lavage), gastrointestinal track (gastrointestinal lavage), colon (colonic lavage), vagina, bladder (bladder irrigation), breast duct (ductal lavage), oral, nasal, sinus cavities, and peritoneal cavity (peritoneal cavity perfusion). In some embodiments the sample or samples are blood or derived from blood.

Purification/Isolation of Sequencing Material

Often, to prepare a sample for determination of the sequence of genetic information contained therein, it is first required to first isolate and/or purify the genetic material away from other sample components. Many methods are known and commonly in use for purifying nucleic acid material from a sample. (See, for instance, Kennedy, Suzanne, "Isolation of DNA and RNA from soil using two different methods optimized with Inhibitor Removal Technology® (IRT)," *BioTechniques*, p. 19, November 2009; Molecular Cloning—A Laboratory Manual (Fourth Edition), M. Green and J. Sambrook, Cold Spring Harbor Laboratory Press, US, 2012; Methods and Tools in Biosciences and Medicine, Techniques in molecular systematics and evolution, R. DeSalle et al. Ed., 2002, Birkhäuser Verlag Basel/Switzerland; Keb-Llanes et al., *Plant Molecular Biology Reporter*, 20:299a-299e, 2002).

Amplification/Enrichment of Target Material

Various platform-specific, or instrument-specific, modifications of the obtained genetic material are often required prior to sequencing. (See, Berglund et al., pages 3-5). For most sequencing applications, 1 to 5 micrograms of purified genetic material is needed. Often, amplification of the purified genetic material is needed prior to beginning any sequence determination protocol. Methods for amplification of genetic material, including whole genome amplification (WGA), are known in the art. (See, for instance, Lovmar et al., "Multiple displacement amplification to create a long-lasting source of DNA for genetic studies," *Hum. Mutat.*, 27:603-614, 2006). Amplification of target polynucleotides may employ any of a number of widely-available PCR techniques and non-PCR techniques including, but not limited to, emPCR, rolling circle PCR, transcription mediated amplification to target both RNA and DNA for amplification, nucleic acid sequence based amplification (NASBA) for constant temperature amplification, helicase-dependent isothermal amplification, strand displacement amplification (SDA), Q-beta replicase-based methodologies, ligase chain reaction, loop-mediated isothermal amplification (LAMP), and reaction déplacement chimeric (RDC).

Targeted sequencing is often used as a strategy to simplify genetic samples. In this process, uninteresting or unwanted genetic materials are first removed from the purified sample prior to initiating the sequencing process, a process commonly referred to as target enrichment. (See, Turner et al., "Methods for genomic partitioning," *Annual Rev. Genomics Hum. Genet.*, 10:263-284, 2009; Johansson et al., "Targeted resequencing of candidate genes using selector probes," *Nuc. Acids Res.*, 39:e8, 2011; Kiialainen et al., "Performance of microarray and liquid based capture methods for target enrichment for massively parallel sequencing and SNP discovery," *PLoS Genet.*, 7:e1002027, 2011; and Caruccio N., "Preparation of next-generation sequencing libraries using Nextera™ technology: simultaneous DNA fragmentation and adapter tagging by in vitro transposition," *Methods Mol. Biol.*, 733:241-255, 2011). Other technologies, such as single molecule sequencing technologies, do not require prior amplification of the target.

Fragmentation of Target Material

Fragmentation of the polynucleotides is also often necessary prior to utilization of the various sequencing methods. These methods are well known and published, including sonication, nebulization, hydro-shearing and shearing by other mechanical means such as by use of beads, needle shearing, French pressure cells, and acoustic shearing, etc., restriction digest, and other enzymatic methods such as use of various combinations of nucleases (DNAse, exonucleases, endonucleases, etc.), as well as transposon-based methods. (See, Knierim et al., "Systematic Comparison of Three Methods for Fragmentation of Long-Range PCR Products for Next Generation Sequencing," *PLoS One*, 6(11): e28240, 2011; Quail, M. A., "DNA: Mechanical Breakage," Nov. 15, 2010, eLS; Sambrook, J., "Fragmentation of DNA by Nebulization," *Cold Spring Harb. Protoc.*, doi:10.1101/pdb.prot4539, 2006). Generally, the goal is to obtain polynucleotides of a base pair (bp) size range that is amenable to the sequencing method chosen. For instance, the fragments may be 100 bp, 200 bp, 300 bp, 400 bp, 500 bp, 600 bp, 700 bp, 800 bp, 900 bp, 1000 bp, 1100 bp, 1200 bp, 1300 bp, 1400 bp, 1500 bp or more.

Final Processing of Target Material

Following amplification and/or enrichment, various adapter primers are optionally ligated to the ends of the fragments to be sequenced. Each manufacturer of each instrument type provides their own, often proprietary, adapters and primers specific to their platform and methodologies. To enable ligation, fragments often require polishing or other minor modifications to enable the primers to be ligated. Again, each manufacturer often provides their own suggested protocols specific to their methodologies for preparing the fragments for ligation and use on their platforms.

Imaging Systems—Detection

Imaging of detectable signals emanating from the polymerase activity, i.e. covalent attachment of the next nucleotide in the growing strand complementary to the target polynucleotide, is accomplished through use of highly sensitive optical devices, such as CCD (charge-coupled device) cameras, confocal imaging, total internal reflection fluorescence (TIRF), zero-mode waveguide, and the like. (See, Metzker, *Nat. Rev. Genet.* 11:31-46, 2009). The type of imaging utilized will depend largely on the instrument employed in the present reactions. As discussed above, the user has several different options from which to choose in terms of instrumentation and optical imaging.

Generally, it is desirable for the detectable signal to arise upon incorporation of the next nucleotide in the growing DNA strand by the polymerase enzyme. The incorporated nucleotide in sequential reversible termination reactions would be labeled (discussed in more detail, below) and include a blocking group which prevents further catalysis by the polymerase enzyme beyond the incorporation of the single labeled nucleotide analog. There is contemplated one or more wash steps between incubation with the nucleotide analogs and polymerase incorporation thereof into the growing strand. Washing steps are used to remove any non-incorporated labeled nucleotide analogs after polymerase activity. After signal detection, the incorporated nucleotide is modified, preferably enzymatically, to allow the polymerase to continue catalyzing strand elongation, and incorporation of the next nucleotide analog, ad infinitum, or until the polymerase can no longer read the template. Alternatively, some instruments are capable of continuously performing these reactions so that signals of incorporation appear and are detected in real time. (See, for instance, Thompson et al., "The properties and applications of single-molecule DNA sequencing," *Genome Biol.,* 12:217-227, 2011, especially at FIG. 2).

Some current instruments utilize TIRF, allowing four color detection (one color for each nucleotide, A, T, G and C). TIRF is used in instruments generally employing two (or more) lasers to excite the fluorophores attached to the nucleotide analogs. In TIRF, a narrow evanescent field of light is creating in which the intensity of the light decays exponentially away from the glass surface, allowing only detection of dyes (labels) in the TIRF evanescent field to fluoresce and be detected. (See, Thompson et al.).

Zero mode waveguide (ZMW) is another method of detection employed by some instruments utilizing SBS methodologies, as explained in further detail below. ZMW techniques employ ZMW nanostructures which possess sub-wavelength holes. These holes are capable of isolating a single polymerase enzyme and allow detection of incorporation of singly-labeled nucleotides into the growing polynucleotide chain. (See, Levine et al., "Zero-mode waveguides for single-molecule analysis at high concentrations," *Science,* 299(5607):682-686, 2003). Differently labeled nucleotide analogs may be utilized as substrates for the DNA polymerase reaction and each incorporation event is observed by use of a highly sensitive confocal imaging system capable of simultaneously detecting incorporation of each of the dN5Ps in each of the ZMW on a microsecond scale.

Other imaging devices are commonly employed in commercially available instrumentation designed specifically for NGS utilizing SBS methodologies. (See, for instance, Ryu et al., *Appl. Phys. Lett.,* 88:171112, 2006; Mico et al., *J. Opt. Image Sci. Vis.,* 25:1115-1129, 2008; and Lundquist et al., *Opt. Lett.,* 33:1026-1028, 2008).

Genetic Data Processing

After the sequence information is obtained, the sequence information must be collated and summarized through bioinformatics techniques to assemble the actual contiguous sequence. The data given by these techniques is extremely large and size and is generally translated from the measured signals into short contiguous sequences which ultimately must be re-assembled into the original sequence found in the original sample. (See, Magi et al., "Bioinformatics for Next Generation Sequencing Data," *Genes,* 1:294-307, 2010; and Homer, Li H., "A survey of sequence alignment algorithms for next-generation sequencing," *Brief Bioinform.,* 11:473-483, 2010). These methods are known and published. Again, most commercially available sequencing platforms and instrumentation companies provide customers with software packages capable of handling the generated data and assembling the target sequence.

Sequencing-by-Synthesis (SBS) and Single-Base-Extension (SBE) Sequencing

Several techniques and approaches are available to achieve high-throughput sequencing. (See, Ansorge; Metzker; and Pareek et al., "Sequencing technologies and genome sequencing," *J. Appl. Genet.,* 52(4):413-435, 2011, and references cited therein). The SBS method is a commonly employed technique, coupled with improvements in PCR, such as emulsion PCR (emPCR), to rapidly and efficiently determine the sequence of many fragments of a nucleotide sequence in a short amount of time. In SBS, nucleotides are incorporated by a polymerase enzyme and because the nucleotides are differently labeled, the signal of the incorporated nucleotide, and therefore the identity of the nucleotide being incorporated into the growing synthetic polynucleotide strand, are determined by sensitive instruments, such as cameras, or CCD cameras.

SBS methods commonly employ reversible terminator nucleic acids, i.e. bases which contain a covalent modification precluding further synthesis steps by the polymerase enzyme once incorporated into the growing stand. This covalent modification can then be removed, for instance using chemicals or specific enzymes, to allow the next complementary nucleotide to be added by the polymerase. Other methods employ sequencing-by-ligation techniques, such as the Applied Biosystems SOLiD platform technology. (Id.). Other companies, like Helicos, provide technologies that are able to detect single molecule synthesis in SBS procedures without prior sample amplification, through use of very sensitive detection technologies and special labels that emit sufficient light for detection. Pyrosequencing is another technology employed by some commercially available NGS instruments. The Roche Applied Science 454 GenomeSequencer, involves detection of pyrophosphate (pyrosequencing). (See, Nyren et al., "Enzymatic method for continuous monitoring of inorganic pyrophosphate synthesis," *Anal. Biochem.,* 151:504-509, 1985; see also, US Patent Application Publication Nos. 2005/0130173, 2006/0134633; U.S. Pat. Nos. 4,971,903, 6,258,568 and 6,210,891).

And yet other companies, such as Oxford Nanopore, are planning to launch new instrument platforms based on other, non-synthetic, technologies. (See, Oxford Nanolab press release of Feb. 17, 2013, "Oxford Nanopore introduces DNA 'strand sequencing' on the high-throughput GridION platform and presents MinION, a sequencer the size of a USB memory stick"). The Oxford Nanolabs technology relies on "lab on a chip" technology whereby a single protein nanopore integrated into a lipid bilayer across a microwell is supplied with electrodes for sensing the transmission of a single DNA molecule (or RNA or protein) through the pore at a rate of about 20 ms per residue. Each nucleotide causes a unique and differentially detectable disruption of the electrical current across the microwell, enabling identification of the nucleotide as it passes through the nanopore. Several different enzymes are used to assist and regulate the movement of the nucleotide strand through the nanopore.

(See, Niedringhaus et al., "Landscape of Next-Generation Sequencing Technologies," *Anal. Chem.*, 83:4327-4341, at pages 4336-4337, 2011).

These, and other so-called "Third Generation Sequencing" technologies, have begun to emerge in which sequence information is obtained in real time and employ real-time synthesis strategies. (See, Niedringhaus et al.). Another example of this Third Generation Sequencing method is an instrument commercialized by Pacific Bioscience which is capable of detecting the activity of a single DNA polymerase enzyme. Companies developing such instruments rely on scanning tunneling electron microscopy (TEM), fluorescence resonance energy transfer (FRET), ion-sensitive field effect transistors (ISFETs), single molecule detection and use of newer technology such as protein nanopores and DNA nanoballs. (Id. at page 4328).

However, these third generation and SMRT technologies still in development are believed to be somewhat risky and unproven technologies. The sequencing methodologies experiencing the most commercialization and application in the field are largely SBS-based, utilizing instrumentation and technology surrounding SBS-based protocols. In fact, two of the three most widely used platforms in research today use a synthesis-based methodology. (See, Berglund et al., "Next-generation sequencing technologies and applications for human genetic history and forensics," *Invest. Gen.*, 2(23), 1-15, 2011). Many of these protocols require the use of reversible terminator nucleotide analogs.

Sequencing using the presently disclosed reversible terminator molecules may be performed by any means available. Generally, the categories of available technologies include, but are not limited to, sequencing-by-synthesis (SBS), sequencing by single-base-extension (SBE), sequencing-by-ligation, single molecule sequencing, and pyrosequencing, etc. The method most applicable to the present compounds, compositions, methods and kits is SBS. Many commercially available instruments employ SBS for determining the sequence of a target polynucleotide. Some of these are briefly summarized below.

One method, used by the Roche Applied Science 454 GenomeSequencer, involves detection of pyrophosphate (pyrosequencing). (See, Nyren et al., "Enzymatic method for continuous monitoring of inorganic pyrophosphate synthesis," *Anal. Biochem.*, 151:504-509, 1985). As with most methods, the process begins by generating nucleotide fragments of a manageable length that work in the system employed, i.e. about 400-500 bp. (See, Metzker, at page 32). Nucleotide primers are ligated to either end of the fragments and the sequences individually amplified by binding to a bead followed by emulsion PCR. The amplified DNA is then denatured and each bead is then placed at the top end of an etched fiber in an optical fiber chip made of glass fiber bundles. The fiber bundles have at the opposite end a sensitive charged-couple device (CCD) camera to detect light emitted from the other end of the fiber holding the bead. Each unique bead is located at the end of a fiber, where the fiber itself is anchored to a spatially-addressable chip, with each chip containing hundreds of thousands of such fibers with beads attached. Next, using an SBS technique, the beads are provided a primer complementary to the primer ligated to the opposite end of the DNA, polymerase enzyme and only one native nucleotide, i.e., C, or T, or A, or G, and the reaction allowed to proceed. Incorporation of the next base by the polymerase releases light which is detected by the CCD camera at the opposite end of the bead. (See, Ansorge, at page 196). The light is generated by use of an ATP sulfurylase enzyme, inclusion of adenosine 5' phosphosulferate, luciferase enzyme and pyrophosphate. (See, Ronaghi, M., "Pyrosequencing sheds light on DNA sequencing," *Genome Res.*, 11(1):3-11, 2001).

A commercially available instrument, called the Genome Analyzer, also utilizes SBS technology. (See, Ansorge, at page 197). Similar to the Roche instrument, sample DNA is first fragmented to a manageable length and amplified. The amplification step is somewhat unique because it involves formation of about 1000 copies of single-stranded DNA fragments, called polonies. Briefly, adapters are ligated to both ends of the DNA fragments, and the fragments are then hybridized to a surface having covalently attached thereto primers complimentary to the adapters, forming tiny bridges on the surface. Thus, amplification of these hybridized fragments yields small colonies or clusters of amplified fragments spatially co-localized to one area of the surface. SBS is initiated by supplying the surface with polymerase enzyme and reversible terminator nucleotides, each of which is fluorescently labeled with a different dye. Upon incorporation into the new growing strand by the polymerase, the fluorescent signal is detected using a CCD camera. The terminator moiety, covalently attached to the 3' end of the reversible terminator nucleotides, is then removed as well as the fluorescent dye, providing the polymerase enzyme with a clean slate for the next round of synthesis. (Id., see also, U.S. Pat. No. 8,399,188; Metzker, at pages 34-36).

Other methods are available which avoid the sample amplification step, such as the Helicos instrument, HeliScope, which allows for single molecule sequencing. This technology still utilizes an SBS approach, wherein flow cells containing glass cover slips are used which have covalently attached primers. The nucleotide material in the sample is still fragmented, as in other technologies, but the amplification step is skipped and the fragmented material is then hybridized to the primers on the glass cover slip in the flow cell. Polymerase enzyme and other necessary components are then added, including differently labeled nucleotides, as in the other SBS strategies. The light emitted upon incorporation of the nucleotide is detected using a very sensitive camera. (See, Ansorge, at pages 198-199, and Braslaysky et al., "Sequence information can be obtained from a single DNA molecule," *Proc. Natl. Acad. Sci. USA*, 100:3960-3964, 2003).

The Pacific Biosciences instruments rely on technology which detects a single growing chain of DNA produced by a single DNA polymerase enzyme, a technology termed "single molecule real-time" (SMRT) sequencing. (Id. at 4330). This company produced a new material called zero-mode waveguide (ZMW) nanostructures, subwavelength holes made on a metal film produced by electron beam lithography and ultraviolet photolithography, which are capable of isolating a single polymerase enzyme and allow detection of incorporation of single fluorescently labeled nucleotides into the growing polynucleotide chain. (See, Levine et al., "Zero-mode waveguides for single-molecule analysis at high concentrations," *Science*, 299(5607):682-686, 2003). Again employing an SBS strategy, differently labeled nucleotide analogs called deoxyribonucleoside pentaphosphates (dN5Ps) are utilized as substrates for the DNA polymerase reaction. Each incorporation event is observed by use of a highly sensitive confocal imaging system capable of simultaneously detecting incorporation of each of the dN5Ps in each of the ZMW on a microsecond scale.

Many SBS strategies rely on detection of incorporation of detectably labeled nucleotides and nucleotide analogs. Such detection may rely on fluorescence or other optical signal, but this is not a requirement. Other technologies available are targeted towards measuring changes in heat and pH surrounding the nucleotide incorporation event. (See, Niedringhaus et al., at page 4334; U.S. Pat. Nos. 7,932,034 and 8,262,900; U.S. Patent Application Publication No. 20090127589; and Esfandyarpour et al., "Structural optimization for heat detection of DNA thermosequencing platform using finite element analysis," *Biomicrofluidics,* 2(2): 024102 (1-11), 2008). Ion Torent, a Life Technologies company, utilizes this technology in their ion sensing-based SBS instruments. In the Ion Torrent instrument, field effect transistors (FETs) are employed to detect minute changes in pH in microwells where the SBS polymerase reaction is occurring. Each well in the microwell array is an individual single molecule reaction vessel containing a polymerase enzyme, a target/template strand and the growing complementary strand. Sequential cycling of the four nucleotides into the wells allows FETs aligned below each microwell to detect the change in pH as the nucleotides are incorporated into the growing DNA strand. FETs convert this signal into a change in voltage, the change being commensurate in magnitude with the total number of nucleotides incorporated in that synthesis step.

In SBS-based NGS methods, reversible terminator nucleotides are key to the success of obtaining the identity of the polynucleotide target sequence in an efficient and accurate manner. The present reversible terminators may be utilized in any of these contexts by substitution for the nucleotides and nucleotide analogs previously described in those methods. That is, the substitution of the present reversible terminators may enhance and improve all of these SBS and SBE methods. The majority of these protocols utilize deoxyribonucleotide triphosphates, or dNTPs. Likewise, the present reversible terminators may be substituted in dNTP form. Other forms of the present reversible terminators useful in other methodologies for sequencing are described hereinbelow.

Reversible Terminator Nucleotides and Nucleosides

The process for using reversible terminator molecules in the context of SBS, SBE and like methodologies generally involves incorporation of a labeled nucleotide analog into the growing polynucleotide chain, followed by detection of the label, then cleavage of the nucleotide analog to remove the covalent modification blocking continued synthesis. The cleaving step may be accomplished using enzymes or by chemical cleavage. Modifications of nucleotides may be made on the 5' terminal phosphate or the 3' hydroxyl group. Developing a truly reversible set of nucleotide terminators has been a goal for many years. Despite the recent advances only a few solutions have been presented, most of which cause other problems, including inefficient or incomplete incorporation by the polymerase, inefficient or incomplete cleavage of the removable group, or harsh conditions needed to for the cleaving step causing spurious problems with the remainder of the assay and/or fidelity of the target sequence. In a standard SBS protocol using reversible terminators, the polymerase enzyme has to accommodate obtrusive groups on the nucleotides that are used for attachment of fluorescent signaling moiety, as well as blocking groups on the 3'-oxygen. Native polymerases have a low tolerance for these modifications, especially the 3'-blocking groups. Mutagenesis of polymerase enzymes is necessary to obtain enzymes with acceptable incorporation efficiencies. After cleaving the fluorophore from the base, many current methodologies leave an unnatural "scar" on the remaining nucleobase. (See, for instance, Metzker, Michael A., "Sequencing technologies—the next generation," *Nature Rev. Gen.,* 11:31-46, 2010 and Fuller et al., "The challenges of sequencing by synthesis," *Nat. Biotech.,* 27(11):1013-1023, 2009).

Thus, a limited number of groups suitable for blocking the 3'-oxygen have been shown to be useful when used in combination with certain mutant polymerases which allow the enzyme to tolerate modifications at the 3'-position. These include azidomethyl, allyl and allyloxycarbonyl. (See, for example, Metzker et al., "Termination of DNA synthesis by novel 3'-modified deoxyribonucleoside triphosphates," *Nucleic Acids Res.,* 22:4259-4267, 1994; and U.S. Pat. Nos. 5,872,244; 6,232,465; 6,214,987; 5,808,045; 5,763,594, and 5,302,509; and U.S. Patent Application Publication No. 20030215862). These groups require the application of chemical reagents to effect cleavage. Carboxylic esters, carbonates or thiocarbonate groups at the 3'-position have proven too labile to be effective as chain terminators, ostensibly due to an intrinsic editing activity of the polymerase distinct from exonuclease activity. (See, Canard B & Sarfati R., "DNA polymerase fluorescent substrates with reversible 3'-tags," *Gene,* 148:1-6, 1994).

Reported attempts to utilize deoxynucleotide 5'-triphosphates with 3'-phosphate monoester blocking groups as terminators have not been successful, likely due to a combination of instability, and difficult preparation and purification protocols. (U.S. Pat. No. 6,232,465, and Applicant's unpublished results, and Fuller et al., "The challenges of sequencing by synthesis," *Nat. Biotech.,* 27(11):1013-1023, 2009). To date, incorporation by polymerases or blocking of extension by polymerases using 3'-phosphate nucleotides has heretofor not been demonstrated.

Reversible terminators in the present disclosure comprise a phosphate diester group at the 3' oxygen of the sugar moiety. The 3' phosphate diester may optionally also comprise a linker and/or a labeling moiety, as defined below. Reversible terminator nucleotides of this type are useful in methodologies for determining the sequence of polynucleotides. The methodologies in which these reversible terminator nucleotides are useful include, but are not limited to, automated Sanger sequencing, NGS methods including, but not limited to, sequencing by synthesis, and the like. Virtually any known method of analyzing or detecting a polynucleotide may optionally employ the presently disclosed reversible terminator nucleotides. Such methods may optionally employ a solid substrate to which the template is covalently bound. The solid substrate may be a particle or microparticle or flat, solid surface of the type used in current instrumentation for sequencing of nucleic acids. (See, for example, Ruparel et al., *Proc. Natl. Acad. Sci.,* 102:5932-5937, 2005; EP 1,974,057; WO 93/21340 and U.S. Pat. Nos. 5,302,509 and 5,547,839, and references cited therein). Optionally, the sequencing reaction employing the presently disclosed reversible terminator nucleotides may be performed in solution or the reaction is performed on a solid phase, such as a microarray or on a microbead, in which the DNA template is associated with a solid support. Solid supports may include, but are not limited to, plates, beads, microbeads, whiskers, fibers, combs, hybridization chips, membranes, single crystals, ceramics, and self-assembling monolayers and the like. Template polynucleic acids may be attached to the solid support by covalent binding such as by conjugation with a coupling agent or by non-covalent binding such as electrostatic interactions, hydrogen bonds or antibody-antigen coupling, or by combinations thereof. There are a wide variety of known methods of attaching nucleic acids to solid supports.

In one aspect, reversible terminator nucleotides and nucleosides are provided. The reversible terminators comprise one or more nucleotide 5' phosphates. The number of 5'-phosphates can vary from none, to 1, 2, 3, 4 and as many as 5 or more. The reversible terminator may be a nucleoside or nucleotide. All types of nucleosides are contemplated, including, but not limited to, G, C, A, T and U, as well as rare forms, such as, Inosine, Xanthosine, 7-methylguanosine, dihydrouridine, 5-methylcytosine, and pseudouridine, including methylated forms of G, A, T, and C, and the like. (See, for instance, Korlach et al., "Going beyond five bases in DNA sequencing," Curr. Op. Struct. Biol., 22(3):251-261, 2012, and U.S. Pat. No. 5,646,269, especially columns 17-19).

The reversible terminators disclosed herein comprise a removable blocking group at the 3' oxygen. The removable blocking group may be an alkyl or aryl phosphate diester group. The blocking groups are designed to be removable. In other words, the blocking group is covalently bound to the nucleotide/nucleoside analog but is capable of being hydrolyzed or otherwise removed by any known means. For instance, most commonly such blocking groups may be hydrolyzed chemically or photochemically, or the blocking group may be more specifically removed enzymatically.

These reversible terminator nucleotide analogs are substrates for DNA or RNA polymerases which are able to tolerate the non-native alkyl/aryl phosphate blocking groups attached the 3' oxygen while allowing the polymerase enzyme to incorporate them efficiently and specifically into primer-template complexes. Once incorporated, the reversible terminator nucleotide analogs act as chain terminators precluding further processing by the polymerase enzyme because the blocking groups prevent further polymerase activity. In other words, the polymerase enzyme cannot utilize the modified nucleotide efficiently as a substrate to continue synthesis.

As described in the SBS and SBE methods, above, upon binding to a polymerase and addition to the growing polynucleotide chain, which grows in the 5' to 3' direction, the triphosphate moiety on the 5' end of the molecule is cleaved by the polymerase enzyme, thereby releasing sufficient energy to covalently link it to the free 3' hydroxyl group of the growing polynucleotide chain. If the 5' group in this molecule contained a label or perhaps a quenching molecule, this molecule would be released into solution as, for instance, pyrophosphate and washed away from the reaction chamber. Thus, the label that may optionally be present on the 3' end of the molecule may be visible since it is now covalently attached to the growing polynucleotide chain. After detection, the label may be removed.

However, if the 3' hydroxyl of the reversible terminator molecule does not contain a blocking group, the polymerase enzyme would simply carry on, adding the next available nucleotide to the growing chain. By incorporating a blocking group, the polynucleotide is not capable of continuing further and the reaction pauses.

The reaction may comprise molecules of each dNTP such that each dNTP is distinguishably labeled, i.e. each dNTP has covalently attached thereto a label, or dye molecule, allowing it to be detected. Not only will the incorporated molecule then be detected upon attachment to the growing polynucleotide chain, its identity will be known based on the type of label on the molecule. Such methods are often termed "four color" assays, whereby each of the four dNTP molecules are labeled with a different color allowing them to be distinguished using optical instrumentation, such as CCD cameras and the like.

Alternatively, in SBE type methods, only a single species of reversible terminator molecule is fed into the system at a time, such that only, for instance, cytosine analogs are incorporated first, and the reaction paused to detect its incorporation. Then this first molecule is followed by a different dNTP, such as guanine, and the reaction paused again to allow its detection upon incorporation by way of the many different methods described above for SBE. In such assays, a label is not necessary. Incorporation may be detected by ligation, change in pH, change in temperature, change in voltage conductance, fluorescence or other detectable change in physical or chemical property. However, a blocking group may still be required to pause the reaction a sufficient amount of time to allow detection and recordation of the event.

Thus, the reversible terminators presently disclosed also may optionally include one or more labels or dyes covalently or otherwise associated therewith. The labels may be present on the 3' and/or 5' oxygen and may be located on any of the phosphate moieties such that release of the blocking group yields a signal and/or incorporation of the reversible terminator into a growing polynucleotide strand yields a detectable signal.

When the reversible terminator comprises two labels or dyes, the two labels or dyes may optionally quench each other. There are known label or dye pairs that quench the detectable signal when they are in close proximity to each other. (See, Marras, S A E, "Selection of Fluorophore and Quencher Pairs for Nucleic Acid Hybridization Probes," Methods Molec. Biol., 335:3-16, 2006, and references cited therein). In the present reversible terminator analogs, one of the pair may be located on the 5' end of the molecule and the other on the blocking group on the 3' end, for instance. Upon release of the reversibly bound blocking group, a detectable signal is produced, as depicted in FIG. 1. In one preferred embodiment, D1 is a luminescent signaling moiety, and D2 is a luminescence quenching moiety. The luminescent signal from D1 will be strongly suppressed by the proximate quencher D2 in unincorporated nucleotides; however, D1 will luminesce strongly upon incorporation of the nucleotide into the primer extension product, due to release of the quencher D2. This reduces or eliminates the need for imaging systems with high confocality, e.g., Zero Mode Waveguide (ZMW) or Total Internal Reflectance (TIR) technologies, and washing steps, to exclude background fluorescence from unincorporated nucleotides. Mechanisms of fluorescence quenching include, but are not limited to energy transfer and electron transfer. Effective quenchers and methods for synthetically incorporating them into desired positions in nucleotides are well known in the art. (See, Marras).

Reversible terminator nucleotide/nucleoside analogs are provided as depicted in Formulas I-VI:

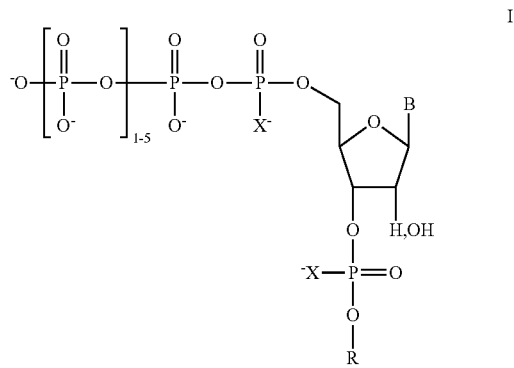

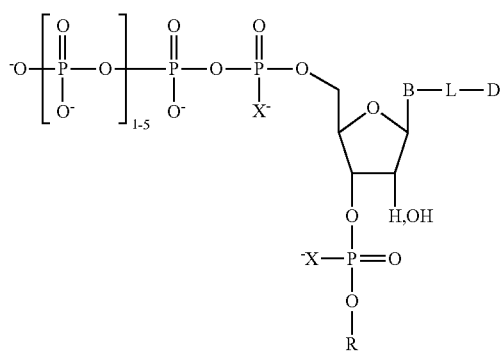

II

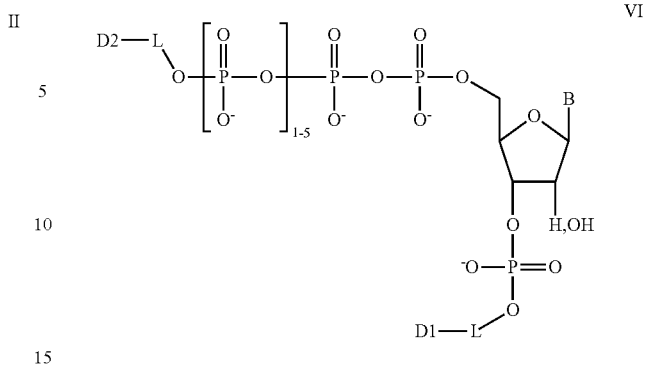

VI wherein:
R=an alkyl or aryl group, optionally substituted
X=O, S, or $BH_3$
B=heterocyclic nucleic acid base
L=optional linker group which is optionally cleavable, in some embodiments L is the blocking group
D1, D2=labels As noted in Formulas I-VI, the 2' position of the sugar moiety may be hydroxyl or hydride, depending on whether the reversible terminator is an RNA or DNA analog, both forms are contemplated. The "R" group is intended to indicate the blocking variable group. However, in some cases the linker "L" may also be the blocking group, especially when combined with D1 and/or D2.

Additionally contemplated are phosphorothioate and boranophosphate modifications of the present reversible terminator molecules. The presence of these modifications can be used to slow the kinetics of the de-blocking steps so that sequencing reactions can be run in a continuous, rather than cyclic mode, i.e., sequential nucleotide additions may be resolved kinetically, such that the process can be monitored in real time.

Another advantage of reversible terminator nucleotides of Formula III and VI, is that a detectable label can be attached to the 3' blocking group. As explained above, for instance when using two labels, a labeled blocking group could be the signal quench and the label present on the 5' end would be the signal emitter. Once the blocking group is removed, simultaneously the quench will also be removed, thereby allowing detection of the signal from the emitter.

In reversible terminators of Formula IV-VI, a label D2 may be attached to the 5' phosphate. In one embodiment, the reversible terminator is an NTP and the D2 label is attached to the gamma phosphate of the NTP analog. Attachment of labels to the gamma phosphate of NTP molecules is well known. (See, Sood et al., *J. Am. Chem. Soc.,* 127:2394-2395, 2005, and Korlach et al., *Nucleot. Nuc. Acids,* 27:1072-1083, 2007). When this analog is used by the polymerase enzyme and incorporated into the growing strand, the triphosphate group will be hydrolyzed, thereby releasing the 5' label into solution. This loss of signal may be detected and directly indicate the incorporation of the reversible terminator nucleotide into the growing polynucleotide strand.

Further, in this embodiment, the separate signaling of two temporally resolvable events is made possible. Nucleotide incorporation may be monitored by release of D2 and loss of signal from D2, and subsequent cleavage and release of D1 from the 3' position, along with the blocking group, will yield a second detectable signal.

While in some embodiments R denotes the reversible blocking group, as in Formula I, II, IV and V, in other

III

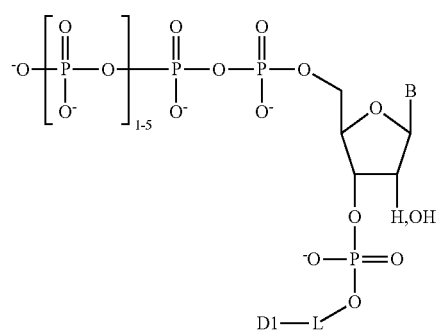

IV

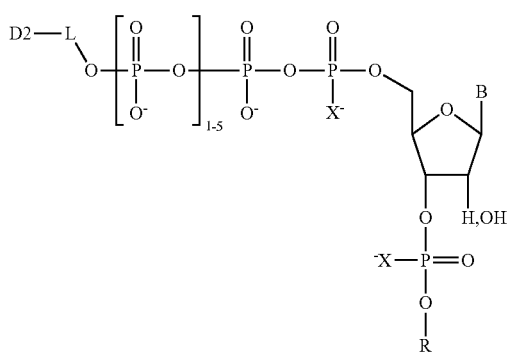

V

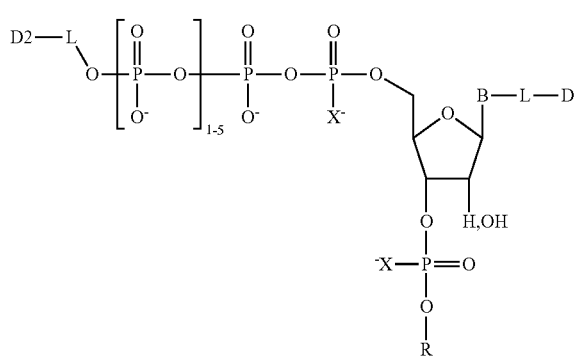

embodiments, the linker group L functions as the reversible blocking group, as in Formula III and VI. That is, both R and L function as reversible blocking groups in that they may be utilized to covalently modify nucleotides/nucleosides at the 3' and/or 5' positions thereby blocking processivity of any polymerase enzyme. They also both optionally possess the capability to be chemically, photochemically and/or enzymatically cleaved in a specific manner without otherwise damaging the core structure or the growing polynucleotide chain being synthesized by the polymerase, or the template polynucleotide.

Linkers

Linkers contemplated herein are of sufficient length and stability to allow efficient hydrolysis or remove by chemical or enzymatic means. Useful linkers will be readily available and capable of reacting with an hydroxyl moiety (or base) on one end of the linker. The opposite end of the linker must be capable of being bound to or modified by a label group, such as D1 and/or D2. The number of carbons, optionally derivatized by other functional groups, must be of sufficient length to allow either chemical or enzymatic cleavage of the blocking group, if the linker is attached to a blocking group.

While precise distances or separation may be varied for different reaction systems to obtain optimal results, in many cases it will be desirable to provide a linkage that maintains the bulky label moiety at some distance away from the nucleotide, e.g., a linker of 1 to 10 nm in length, to reduce steric crowding in enzyme binding sites.

Linkers may be comprised of any number of basic chemical starting blocks. For example, linkers may comprise linear or branched alkyl, alkenyl, or alkynyl chains, or combinations thereof, that provide a useful distance between the sugar group and the label D1 and/or D2. For example, amino-alkyl linkers, e.g., amino-hexyl linkers, have been used to provide label attachment to nucleotide analogs, and are generally sufficiently rigid to maintain such distances. The carbon chain of such linkers may include as many as 2 carbons, 3 carbons, 4 carbons, 5 carbons, 6 carbons, 7 carbons, 8 carbons, 9 carbons or even 10 carbons. The linear or branched linker may also contain heteroatoms other than carbon, including, but not limited to, oxygen, sulfur, phosphate, and nitrogen. A polyoxyethylene chain (also commonly referred to as polyethyleneglycol, or PEG) is a preferred linker constituent due to the hydrophilic properties associated with polyoxyethylene.

The linker may be rigid in nature or flexible. Typically, rigid structures include laterally rigid chemical groups, e.g., ring structures such as aromatic compounds, multiple chemical bonds between adjacent groups, e.g., double or triple bonds, in order to prevent rotation of groups relative to each other, and the consequent flexibility that imparts to the overall linker. Thus, the degree of desired rigidity may be modified depending on the content of the linker, or the number of bonds between the individual atoms comprising the linker. Further, addition of ringed structures along the linker may impart rigidity. Ringed structures may include aromatic or non-aromatic rings. Rings may be anywhere from 3 carbons, to 4 carbons, to 5 carbons or even 6 carbons in size. Rings may also optionally include heteroatoms such as oxygen or nitrogen and also be aromatic or non-aromatic. Rings may additionally optionally be substituted by other alkyl groups and/or substituted alkyl groups.

Linkers that comprise ring or aromatic structures can include, for example aryl alkynes and aryl amides. Other examples of the linkers of the invention include oligopeptide linkers that also may optionally include ring structures within their structure.

For example, in some cases, polypeptide linkers may be employed that have helical or other rigid structures. Such polypeptides may be comprised of rigid monomers, which derive rigidity both from their primary structure, as well as from their helical secondary structures, or may be comprised of other amino acids or amino acid combinations or sequences that impart rigid secondary or tertiary structures, such as helices, fibrils, sheets, or the like. By way of example, polypeptide fragments of structured rigid proteins, such as fibrin, collagen, tubulin, and the like may be employed as rigid linker molecules.

Exemplary linkers are as depicted in Scheme I, below:

Scheme I $$*-[\Phi-[\equiv\!\!\!\equiv\!\!\!\equiv-CH_2]_{0-1}]_{0-1}-[CH_2]_m-Q-[CH_2]_n-[CH_2-O-CH_2]_p-[CH_2]_q-Q-[\underset{H_2}{C}]_{n'}-[CH_2-O-CH_2]_{p'}-[\underset{H_2}{C}]_{q'}-Q-D$$

wherein:

m=0 to 9 n and n'=1 or 2 p and p'=0 to 18 q and q'=1 to 2

D=detectable label

Φ=cyclic structure including aromatic, heterocyclic and fused ring structures

Q=an optional connecting group, which may be, for example, any one or more of the following moieties: —O—, —S—S—, and/or

[triazole ring structure N=N–N–], and [—X—C(O)—Y—];

where X and Y are O, S, NH$_2$, or CH$_2$, and

[triazole ring structure N=N–N–].

Non-limiting examples of linkers of the present invention are:

—(CH$_2$)$_6$—NHC(O)(CH$_2$)$_n$—NHC(O)—

—CH$_2$(CH$_2$OCH$_2$)$_3$CH$_2$—NHC(O)—(CH$_2$)$_n$—NHC(O)—

—CH$_2$CH(CH$_2$CH$_2$OH)(OCH$_2$CH$_2$)$_n$—NHC(O)—(CH$_2$)$_n$—NHC(O)—

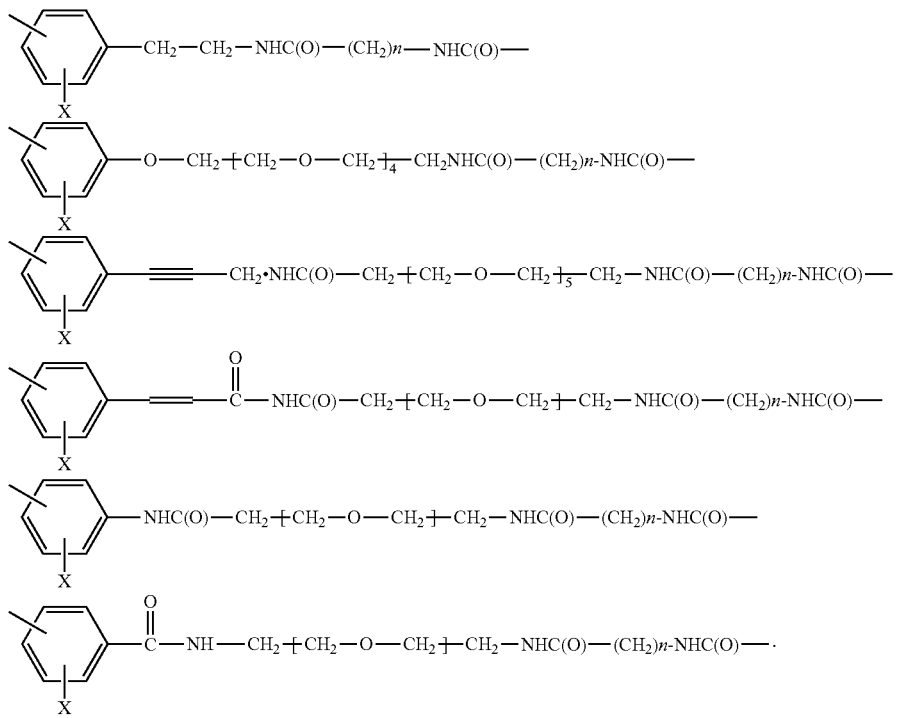

(X = optional substituent, eg., halogen)

Reversible Terminator Labels & Dyes

A label, as in D, D1 and/or D2, of the present reversible terminators, may be any moiety that comprises one or more appropriate chemical substances or enzymes that directly or indirectly generate a detectable signal in a chemical, physical or enzymatic reaction. If at least two label components are present in a given label, based on its particular properties each label component may be differentially detectable. A large variety of labels are well known in the art. (See, for instance, PCT/GB2007/001770).

For instance, one class of such labels are fluorescent labels. Fluorescent labels have the advantage of coming in several different wavelengths (colors) allowing distinguishably labeling each different terminator molecule. (See, for example, Welch et al., Chem. Eur. J., 5(3):951-960, 1999). One example of such labels are dansyl-functionalized fluorescent moieties. Another example are the fluorescent cyanine-based labels Cy3 and Cy5, which can also be used in the present invention. (See, Zhu et al., Cytometry, 28:206-211, 1997). Labels suitable for use are also disclosed in Prober et al., Science, 238:336-341, 1987; Connell et al., BioTechniques, 5(4):342-384, 1987; Ansorge et al., Nucl. Acids Res., 15(11):4593-4602, 1987; and Smith et al., Nature, 321:674, 1986. Other commercially available fluorescent labels include, but are not limited to, fluorescein and related derivatives such as isothiocyanate derivatives, e.g. FITC and TRITC, rhodamine, including TMR, texas red and Rox, bodipy, acridine, coumarin, pyrene, benzanthracene, the cyanins, succinimidyl esters such as NHS-fluorescein, maleimide activated fluorophores such as fluorescein-5-maleimide, phosphoramidite reagents containing protected fluorescein, boron-dipyrromethene (BODIPY) dyes, and other fluorophores, e.g. 6-FAM phosphoramidite 2. All of these types of fluorescent labels may be used in combination, in mixtures and in groups, as desired and depending on the application.

Various commercially available fluorescent labels are known in the art, such as Alexa Fluor Dyes, e.g., Alexa 488, 555, 568, 660, 532, 647, and 700 (Invitrogen-Life Technologies, Inc., California, USA, available in a wide variety of wavelengths, see for instance, Panchuk, et al., J. Hist. Cyto., 47:1179-1188, 1999). Also commercially available are a large group of fluorescent labels called ATTO dyes (available from ATTO-TEC GmbH in Siegen, Germany). These fluorescent labels may be used in combinations or mixtures to provide distinguishable emission patterns for all terminator molecules used in the assay since so many different absorbance and emission spectra are commercially available.

In various exemplary embodiments, a label comprises a fluorescent dye, such as, but not limited to, a rhodamine dye, e.g., R6G, R1 10, TAMRA, and ROX, a fluorescein dye, e.g., JOE, VIC, TET, HEX, FAM, etc., a halo-fluorescein dye, a cyanine dye. e.g., CY3, CY3.5, CY5, CY5.5, etc., a BODIPY® dye, e.g., FL, 530/550, TR, TMR, etc., a dichlororhodamine dye, an energy transfer dye, e.g., BIGD YE™ v 1 dyes, BIGD YE™ v 2 dyes, BIGD YE™ v 3 dyes, etc., Lucifer dyes, e.g., Lucifer yellow, etc., CASCADE BLUE®, Oregon Green, and the like. Other exemplary dyes are provided in Haugland, Molecular Probes Handbook of Fluorescent Probes and Research Products, Ninth Ed. (2003) and the updates thereto. Non-limiting exemplary labels also include, e.g., biotin, weakly fluorescent labels (see, for instance, Yin et al., Appl Environ Microbiol., 69(7):3938, 2003; Babendure et al., Anal. Biochem., 317(1):1, 2003; and Jankowiak et al., Chem. Res. Toxicol., 16(3):304, 2003), non-fluorescent labels, colorimetric labels, chemiluminescent labels (see, Wilson et al., Analyst, 128(5):480, 2003; Roda et al., Luminescence, 18(2):72, 2003), Raman labels, electrochemical labels, bioluminescent labels (Kitayama et al., Photochem. Photobiol., 77(3):333, 2003; Arakawa et al., Anal. Biochem., 314(2):206, 2003; and Maeda, J. Pharm. Biomed. Anal., 30(6): 1725, 2003), and the like.

Multiple labels can also be used in the invention. For example, bi-fluorophore FRET cassettes (Tet. Letts., 46:8867-8871, 2000) are well known in the art and can be utilized in the disclosed methods. Multi-fluor dendrimeric systems (J. Amer. Chem. Soc., 123:8101-8108, 2001) can also be used. Other forms of detectable labels are also available. For example, microparticles, including quantum dots (Empodocles, et al., Nature, 399:126-130, 1999), gold nanoparticles (Reichert et al., Anal. Chem., 72:6025-6029, 2000), microbeads (Lacoste et al., Proc. Natl. Acad. Sci. USA, 97(17):9461-9466, 2000), and tags detectable by mass spectrometry can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

Thus, a "label" as presently defined is a moiety that facilitates detection of a molecule. Common labels in the context of the present invention include fluorescent, luminescent, light-scattering, and/or colorimetric labels. Suitable labels may also include radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. As other non-limiting examples, the label can be a luminescent label, a light-scattering label (e.g., colloidal gold particles), or an enzyme (e.g., Horse Radish Peroxidase (HRP)).

Fluorescence energy transfer (FRET) dyes may also be employed, such as DY-630/DY-675 from Dyomics GmbH of Germany, which also commercially supplies many different types of dyes including enzyme-based labels, fluorescent labels, etc. (See, for instance, Dohm et al., "Substantial biases in ultra-short read data sets from high-throughput DNA sequencing," Nucleic Acids Res., 36:e105, 2008). Other donor/acceptor FRET labels include, but are not limited to:

| Donor | Acceptor | $R_0$ (Å) |
|---|---|---|
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 and QSY 9 dyes | 61 |

(See also, Johansen, M. K., "Choosing Reporter-Quencher Pairs for Efficient Quenching Through Formation of Intramolecular Dimers," Methods in Molecular Biology, vol. 335: Fluorescent Energy Transfer Nucleic Acid Probes: Designs and Protocols, Edited by: V. V. Didenko, Humana Press Inc., Totowa, N.J.). Other dye quenchers are commercially available, including dabcyl, QSY quenchers and the like. (See also, Black Hole Quencher Dyes from Biosearch Technologies, Inc., Novato, Calif.; Iowa Black Dark Quenchers from Integrated DNA Technologies, Inc. of Coralville, Iowa; and other dye quenchers sold by Santa Cruz Biotechnology, Inc. of Dallas, Tex.).

The label and linker construct can be of a size or structure sufficient to act as a block to the incorporation of a further nucleotide onto the nucleotide of the invention. This permits controlled polymerization to be carried out. The block can be due to steric hindrance, or can be due to a combination of size, charge and structure.

Polymerase Enzymes for Use in SBS/SBE Sequencing

As already commented upon, one of the key challenges facing SBS or SBE technology is finding reversible terminator molecules capable of being incorporated by polymerase enzymes efficiently and which provide a blocking group that can be removed readily after incorporation. Thus, to achieve the presently claimed methods, polymerase enzymes must be selected which are tolerant of modifications at the 3' and 5' ends of the sugar moiety of the nucleoside analog molecule. Such tolerant polymerases are known and commercially available.

Preferred polymerases lack 3'-exonuclease or other editing activities. As reported elsewhere, mutant forms of 9° N-7(exo-) DNA polymerase can further improve tolerance for such modifications (WO 2005024010; WO 2006120433), while maintaining high activity and specificity. An example of a suitable polymerase is THERMINATORT™ DNA polymerase (New England Biolabs, Inc., Ipswich, Mass.), a Family B DNA polymerase, derived from Thermococcus species 9° N-7. The 9° N-7(exo-) DNA polymerase contains the D141A and E143A variants causing 3'-5' exonuclease deficiency. (See, Southworth et al., "Cloning of thermostable DNA polymerase from hyperthermophilic marine Archaea with emphasis on Thermococcus species 9° N-7 and mutations affecting 3'-5' exonuclease activity," Proc. Natl. Acad. Sci. USA, 93(11): 5281-5285, 1996). THERMINATORT™ I DNA polymerase is 9° N-7 (exo-) that also contains the A485L variant. (See, Gardner et al., "Acyclic and dideoxy terminator preferences denote divergent sugar recognition by archaeon and Taq DNA polymerases," Nucl. Acids Res., 30:605-613, 2002). THERMINATOR™ III DNA polymerase is a 9° N-7(exo-) enzyme that also holds the L408S, Y409A and P410V mutations. These latter variants exhibit improved tolerance for nucleotides that are modified on the base and 3' position. Another polymerase enzyme useful in the present methods and kits is the exo-mutant of KOD DNA polymerase, a recombinant form of Thermococcus kodakaraensis KOD1 DNA polymerase. (See, Nishioka et al., "Long and accurate PCR with a mixture of KOD DNA polymerase and its exonuclease deficient mutant enzyme," J. Biotech., 88:141-149, 2001). The thermostable KOD polymerase is capable of amplifying target DNA up to 6 kbp with high accuracy and yield. (See, Takagi et al., "Characterization of DNA polymerase from Pyrococcus sp. strain KOD1 and its application to PCR," App. Env. Microbiol., 63(11):4504-4510, 1997). Others are Vent (exo-), Tth Polymerase (exo-), and Pyrophage (exo-) (available from Lucigen Corp., Middletown, Wis., US). Another non-limiting exemplary DNA polymerase is the enhanced DNA polymerase, or EDP. (See, WO 2005/024010).

When sequencing using SBE, suitable DNA polymerases include, but are not limited to, the Klenow fragment of DNA polymerase I, SEQUENASE™ 1.0 and SEQUENASE™ 2.0 (U.S. Biochemical), T5 DNA polymerase, Phi29 DNA polymerase, THERMOSEQUENASE™ (Taq polymerase with the Tabor-Richardson mutation, see Tabor et al., Proc. Natl. Acad. Sci. USA, 92:6339-6343, 1995) and others known in the art or described herein. Modified versions of these polymerases that have improved ability to incorporate a nucleotide analog of the invention can also be used.

Further, it has been reported that altering the reaction conditions of polymerase enzymes can impact their promiscuity, allowing incorporation of modified bases and reversible terminator molecules. For instance, it has been reported that addition of specific metal ions, e.g., $Mn^{2+}$, to polymerase reaction buffers yield improved tolerance for modified nucleotides, although at some cost to specificity (error rate). Additional alterations in reactions may include conducting the reactions at higher or lower temperature, higher or lower pH, higher or lower ionic strength, inclusion of co-solvents or polymers in the reaction, and the like.

Random or directed mutagenesis may also be used to generate libraries of mutant polymerases derived from native species; and the libraries can be screened to select mutants with optimal characteristics, such as improved efficiency, specificity and stability, pH and temperature optimums, etc. Polymerases useful in sequencing methods are typically polymerase enzymes derived from natural sources. Polymerase enzymes can be modified to alter their specificity for modified nucleotides as described, for example, in WO 01/23411, U.S. Pat. No. 5,939,292, and WO 05/024010. Furthermore, polymerases need not be derived from biological systems.

De-Blocking: Removal of the Reversible Terminator Nucleotides

After incorporation, the alkyl/aryl phosphate blocking groups and/or linkers can be removed from the reversible terminator molecules of Formulas I-VI, by various means including, but not limited to, chemical means, photo-cleavage, and enzymatic removal. Removal of the blocking and/or linker group from the 3' and/or 5' position reactivates or releases the growing polynucleotide strand, freeing it to be available for subsequent extension by the polymerase enzyme. This enables the controlled extension of the primers by a single nucleotide in a sequential manner.

The 3' blocking groups disclosed herein are specially designed to allow their removal by enzymatic means, which is sometimes preferred, as opposed to chemical means.

One advantage of enzymatic de-blocking is that it is more efficient and less aggressive towards the nucleic acid substrates, compared with chemical de-blocking steps. This enables longer extension products longer (or read lengths) by maintaining competent strands for a greater number of cycles. Another advantage offered by enzymatic blocking group removal is that it allows single-molecule sequencing reactions to be run in a continuous, rather than cyclic mode, i.e., sequential nucleotide additions may be resolved kinetically, such that the process can be monitored in real time. Moreover, once the blocking group and label are released, the remaining nucleotides are entirely "native" in structure. This is unlike existing terminator nucleotide chemistry that require labels attached to the base. These existing terminator nucleotides leave residual modifications or "scars" on the bases which accumulate in the extended strand as SBS proceeds. The accumulation of these base modifications can interfere with the efficiency and specificity of subsequent cycles of chain extension, thereby limiting the length and quality of the extension products or sequencing reads.

The reversible nucleotide analogs may be cleaved using phospholipase enzymes and/or phosphodiesterases with "AP-lyase" activity, such as the reported "apurinic" endonucleases, e.g., Endonuclease IV and APE-1, and single-strand specific 3'-exonucleases such as Exonuclease-I. These enzymes are known for removing 3'-blocking groups which can result from DNA damage in cells due to certain types of radiation or chemical exposure. Error correcting phosphodiesterases as T7 Endonucleases-I are potentially useful as they recognize and cleave strands at abasic sites, as well as mismatch sites, etc; although they can be somewhat indiscriminate and cleave at multiple sites close to the lesion.

Other potentially useful phosphodiesterases include phospholipases. One species of phospholipase useful in the present methods and kits is phospholipase C (PLC). In the reaction catalyzed by PLC, the nucleoside 3' oxygen would take the place of the diacyl glycerol as substrate. Phospholipase C is a class of enzymes that cleave phospholipids just before the phosphate group. Thirteen kinds of mammalian phospholipase C are classified into six isotypes ($\beta$, $\gamma$, $\delta$, $\epsilon$, $\zeta$, $\eta$) according to structure. Phospholipase D (EC 3.1.4.4, lipophosphodiesterase II, lecithinase D, choline phosphatase, PLD) is an enzyme which is located in the plasma membrane and catalyzes the hydrolysis of phosphatidylcholine to form phosphatidic acid (PA), releasing the soluble choline headgroup into the cytosol. When using the enzyme PLD, the linker "L" of the present invention serves as a mimic for the diacyl glycerol moiety. There are two mammalian isoforms of phospholipase D: PLD1 and PLD2.

Furthermore, random or directed mutagenesis can be used to generate libraries of mutant phosphodiesterases derived from native species. These libraries can be screened to select mutants with optimal characteristics such as improved efficiency, specificity and stability, improved pH and temperature optima, etc. (See, for instance, WO 01/23411, U.S. Pat. No. 5,939,292, WO 05/024010, and US Patent Application Publication No. 20120270253). Random mutagenesis methods include, for example, use of *E. coli* XL1red, UV irradiation, chemical modification such as by deamination, alkylation, or base analog mutagens, or PCR methods such as DNA shuffling, cassette mutagenesis, site-directed random mutagenesis, or error prone PCR (see e.g. U.S. Application No.: 2006-0115874). Such examples include, but are not limited to, chemical modification by hydroxylamine (Ruan, H., et al. (1997) *Gene* 188:35-39), the use of dNTP analogs (Zaccolo, M., et al. (1996) *J. Mol. Biol.* 255:589-603), or the use of commercially available random mutagenesis kits such as, for example, GeneMorph PCR-based random mutagenesis kits (Stratagene) or Diversify random mutagenesis kits (Clontech). The Diversify random mutagenesis kit allows the selection of a desired mutation rate for a given DNA sequence (from 2 to 8 mutations/1000 base pairs) by varying the amounts of manganese (Mn2+) and dGTP in the reaction mixture. Raising manganese levels initially increases the mutation rate, with a further mutation rate increase provided by increased concentration of dGTP. Even higher rates of mutation can be achieved by performing additional rounds of PCR. Other random mutagenesis kits are commercially available, such as the GENEMORPH® II kit from Agilent, Inc. (Santa Clara, Calif.), kits from Jena Bioscience (Jena, Germany), the MGS kit from Fisher Scientific (Pittsburgh, Pa.), and the like.

Modification of the phosphates as phosphorothioates (X=S) or boranophosphates (X=$BH_3$) is known to impart a high degree of resistance towards phosphoesterases. This resistance can provide reductions in unintended interfering activities which may arise from exogenous polymerase, nuclease or other phosphoesterases, as well as from intrinsic nuclease activities. (See, Eckstein, F. "Nucleoside Phosphorothioates," *Ann. Rev. Biochem.*, 54:367-402, 1985; Guga et al., "Phosphorothioate Nucleotides and Oligonucleotides—Recent Progress in Synthesis and Application," *Chemistry & Biodiversity*, 8(9):1642-1681, 2011; Li et al., "Nucleoside and Oligonucleoside Boranophosphates: Chemistry and Properties," *Chem. Rev.*, 107:4746-96, 2007).

Definitions

All terms are intended to be understood as they would be understood by a person skilled in the art. Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "hydroxyl protective group" is intended to include any group which forms a derivative of the hydroxyl group that is stable to the projected reactions wherein said hydroxyl protective group subsequently optionally can be selectively removed. Said hydroxyl derivative can be obtained by selective reaction of a hydroxyl protecting agent with a hydroxyl group.

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra.

The term "polynucleotide" (and the equivalent term "nucleic acid") encompasses any physical string of monomer units that can be corresponded to a string of nucleotides, including a polymer of nucleotides, e.g., a typical DNA or RNA polymer, peptide nucleic acids (PNAs), modified oligonucleotides, e.g., oligonucleotides comprising nucleotides that are not typical to biological RNA or DNA, such as 2'-O-methylated oligonucleotides, and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

The term "analog" in the context of nucleic acid analog is meant to denote any of a number of known nucleic acid analogs such as, but not limited to, LNA, PNA, etc.

The term "aromatic" used in the present application means an aromatic group which has at least one ring having a conjugated pi electron system, i.e., aromatic carbon molecules having 4n+2 delocalized electrons, according to Huckel's rule, and includes both carbocyclic aryl, e.g., phenyl, and heterocyclic aryl groups, e.g., pyridine. The term includes monocyclic or fused-ring polycyclic, i.e., rings which share adjacent pairs of carbon atoms, groups.

The term "aromatic" when used in the context of "aromatic solvent" as used in the present disclosure means any of the known and/or commercially available aromatic solvents, such as, but not limited to, toluene, benzene, xylenes, any of the Kesols, and/or GaroSOLs, and derivatives and mixtures thereof.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated, i.e. $C_1$-$C_{10}$ means one to ten carbon atoms in a chain. Non-limiting examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl."

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CHCH—O—$CH_3$, —Si($CH_3$)$_3$, —$CH_2$—CHN—O$CH_3$, and —CHCH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini, e.g., alkyleneoxy, alkylenedioxy, alkyleneamino, alkylenediamino, and the like. Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring, such as those that follow Hückel's rule (4n+2, where n is any integer), or multiple rings (preferably from 1 to 5 rings), which are fused together or linked covalently and including those which obey Clar's Rule. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms, e.g., aryloxy, arylthioxy, arylalkyl, includes both aryl and heteroaryl rings as defined above. Thus, the term "arylalkyl" is meant to include those radicals in which an aryl group is attached to an alkyl group, e.g., benzyl, phenethyl, pyridylmethyl and the like, including those alkyl groups in which a carbon atom, e.g., a methylene group, has been replaced by, for example, an oxygen atom, e.g., phenoxymethyl, 2-pyridyloxymethyl, 3-(1-naphthyloxy)propyl, and the like.

Each of the above terms, e.g., "alkyl," "heteroalkyl," "aryl" and "heteroaryl," is meant to include both substituted and unsubstituted forms of the indicated radical. Preferred substituents for each type of radical are provided below.

Substituents for the alkyl and heteroalkyl radicals, including those groups often referred to as alkylene, alkenyl, heteroalkylene, heteroalkenyl, alkynyl, cycloalkyl, heterocycloalkyl, cycloalkenyl, and heterocycloalkenyl, are generically referred to as "alkyl group substituents," and they can be one or more of a variety of groups selected from, but not limited to: —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$ in a number ranging from zero to (2M'+1), where M' is the total number of carbon atoms in such radical. R', R'', R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl, e.g., —CF$_3$ and —CH$_2$CF$_3$) and acyl, e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR''', —NR—C(NR'R'')=NR''', —S(O)R', —S(O)$_2$R', —S(O)$_2$NR'R'', —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R'', R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present. In the schemes that follow, the symbol X represents "R" as described above.

Unless otherwise noted, the term "catalytic amount," as used herein, includes that amount of the reactant that is sufficient for a reaction of the process of the invention to occur. Accordingly, the quantity that constitutes a catalytic amount is any quantity that serves to allow or to increase the rate of reaction, with larger quantities typically providing a greater increase. The quantity used in any particular application will be determined in large part by the individual needs of the manufacturing facility. Factors which enter into such a determination include the catalyst cost, recovery costs, desired reaction time, and system capacity. It will be most convenient to use an amount of reactant in the range from about 0.001 to about 0.5 equivalents, from about 0.001 to about 0.25 equivalents, from about 0.01 to about 0.25 equivalents, from about 0.001 to about 0.1, from about 0.01 to about 0.1 equivalents, including about 0.005, about 0.05 or about 0.08 equivalents of the reactant/substrate, or in the range from about 0.001 to about 1 equivalents, from about 0.001 to about 0.5 equivalents, from about 0.001 to about 0.25 equivalents, from about 0.001 to about 0.1 equivalents, from about 0.01 to about 0.5 equivalents or from about 0.05 to about 0.1 equivalents, including about 0.005, about 0.02 or about 0.04 equivalents.

Applicants are aware that there are many conventions and systems by which organic compounds may be named and otherwise described, including common names as well as systems, such as the IUPAC system.

Abbreviations

Abbreviations used throughout the present application have the meanings provided below. The meanings provided below are not meant to be limiting, but are meant to also encompass any equivalent common or systematic names understood by one of skill in the art. The meaning commonly understood by one of skill in the art should be ascribed to any other abbreviated names not listed below.

$I_2$=iodine
Pyr=pyridine base
THF=tetrahydrofuran
TsOH=p-toluene sulfonic acid
DCA=dichloroacetic acid
$Bu_3N$=tributyl amine
DMF=dimethylformamide
Py=pyridine
TEAB=triethylammonium bicarbonate
DMTO=4,4'-dimethoxytriphenylmethoxy
CEO=2-cyanoethoxy
TIPSCl=triisopropylsilyl ether chloride
Et=ethyl
Ph=phenyl
$(PhO)_2P(O)Cl$=diphenylphosphoryl chloride
CEO-P$(NiPr_2)_2$=O-(2-cyanoethyl)-N,N,N,N-tetraisopropylphosphorodiamidite
$iPr_2NH$=diisopropylamine
DBU=1,8-diazabicycloundec-7-ene
FMOC=fluorenylmethyloxycarbonyl
TCEP=(tris(2-carboxyethyl)phosphine)
CDI=1,1'-carbonyldiimidazole
MeOH=methanol
TBA=tert-butyl alcohol or 2-methyl-2-propanol
TEA=triethanolamine
TFP=tetrafluoropropanol or 2,2,3,3-tetrafluoro-1-propanol
BSA=bovine serum albumin
DTT=dithiothreitol
ACN=acetonitrile
NaOH=sodium hydroxide
IE HPLC=ion-exchange high performance liquid chromatography
TLC=thin-layer chromatography Synthetic Methods The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

For instance, in all instances, where a drying agent is used, contemplated drying agents include all those reported in the literature and known to one of skill, such as, but not limited to, magnesium sulfate, sodium sulfate, calcium sulfate, calcium chloride, potassium chloride, potassium hydroxide, sulfuric acid, quicklime, phosphorous pentoxide, potassium carbonate, sodium, silica gel, aluminum oxide, calcium hydride, lithium aluminum hydride (LAH), potassium hydroxide, and the like. (See, Burfield et al., "Dessicant Efficiency in Solvent Drying. A Reappraisal by Application of a Novel Method for Solvent Water Assay," *J. Org. Chem.*, 42(18):3060-3065, 1977). The amount of drying agent to add in each work up may be optimized by one of skill in the art and is not particularly limited. Further, although general guidance is provided for work-up of the intermediates in each step, it is generally understood by one of skill that other optional solvents and reagents may be equally substituted during the work-up steps. However, in some exceptional instances, it was found the very specific work-up conditions are required to maintain an unstable intermediate. Those instances are indicated below in the steps in which they occur.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59). Though certain organic co-solvents and quenching agents may be indicated in the steps described below, other equivalent organic solvents and quenching agents known to one of skill may be employed equally as well and are fully contemplated herein. Further, most of the work-ups in most steps may be further altered according to preference and desired end use or end product. Drying and evaporation, routine steps at the organic synthetic chemist bench, need not be employed and may be considered in all steps to be optional. The number of extractions with organic solvent may be as many as one, two, three, four, five, or ten or more, depending on the desired result and scale of reaction. Except where specifically noted, the volume, amount of quenching agent, and volume of organic solvents used in the work-up may be varied depending on specific reaction conditions and optimized to yield the best results.

Additionally, where inert gas or noble gas is indicated, any inert gas commonly used in the art may be substituted for the indicated inert gas, such as argon, nitrogen, helium, neon, etc.

A number of patents and publications are cited herein in order to more fully describe and disclose the present methods, compounds, compositions and kits, and the state of the art to which they pertain. The references, publications, patents, books, manuals and other materials cited herein to illuminate the background, known methods, and in particular, to provide additional details with respect to the practice of the present methods, compositions and/or kits, are all incorporated herein by reference in their entirety for all purposes, to the same extent as if each individual reference was specifically and individually indicated to be incorporated by reference.

EXAMPLES

General

It is understood that the examples and embodiments described herein are for illustrative purposes and that various modifications or changes in light thereof will be suggested to persons skilled in the art and are to be included within the spirit and purview of this application and scope of the claims. Accordingly, the following examples are offered to illustrate, but not to limit, the claimed invention.

Preparative Methods

The preparation of deoxynucleoside 3'-phosphates with functionalizable blocking and linker groups may proceed as depicted in Scheme II, starting from available nucleoside 3'-O-phosphoramidites or H-phosphonates. The synthetic steps depicted in Scheme II are standard and commonly used published procedures which are well-known to those skilled in the art. The variable groups B, X and L are as defined, above. $B^{pr}$ represents a protected heterocyclic nucleic acid base.

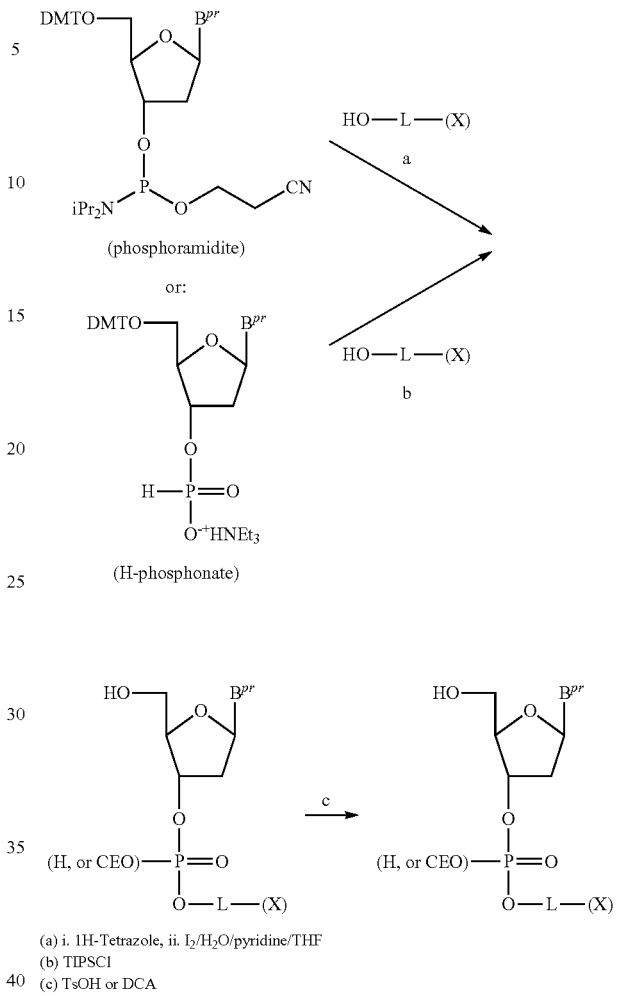

In another approach, the preparation of deoxynucleoside 3'-phosphates with functionalizable blocking/linker groups may proceed as shown in Scheme III. In this case, the functionalizable blocking/linker group HO-L-(X) is first converted to a suitably protected phosphoramidite, H-phosphonate, or phosphodiester intermediate; any of which can then be coupled to the 3'-hydroxyl of suitably protected nucleoside using standard published reagents and protocols commonly used in oligonucleotide synthesis. Again, B, L and X are as defined above.

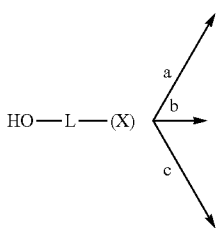

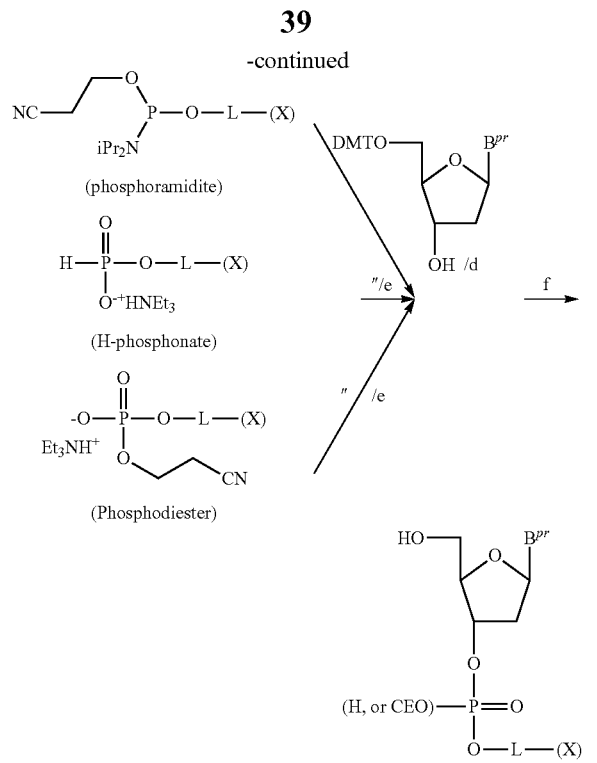

(a) CEO—P(NiPr₂)₂/1H-Tetrazole /iPr₂NH
(b) i. (PhO)₂P(O)H/pyridine, ii. Et₃N/H₂O
(c) i. CEO—P(O)Cl₂/pyridine, ii. H₂O, iii. Et₃N/H₂O
(d) i. 1H-Tetrazole, ii. I₂/H₂O/pyridine/THF
(e) TIPSCl
(f) TsOH or DCA The base-protected 2'-deoxynucleosides, 5'-O-(4,4'-dimethoxytrityl)-2'-deoxynucleosides, 5'-O-DMT-2'-deoxynucleoside-3'-O—(O-(2-cyanoethyl)-N,N-diisopropyl) phosphoramidites, and 5'-O-DMT-2'-deoxynucleoside-3'-O—H-phosphonates, which are depicted in the preceding schemes, are available from a number of commercial sources (Glen Research, Sterling, Va.; ChemGenes, Wilmington, Mass.; ThermoFisher Scientific, Waltham, Mass.; SAFC® PROLIGO® reagents from Sigma-Aldrich, St. Louis, Mo.; etc.). Of the base protecting groups for A, G, and C, which are available, isobutyryl (iBu), phenoxyacetyl (Pac), or (alkylphenoxy)acetyl are generally preferred.

To prepare reversible terminators, the above described base-protected deoxynucleoside 3'-phosphates with attached functionalizable linker, are then converted to 5'-triphosphates using any one of the many published protocols for carrying out this purpose. (See, for instance, Caton-Williams J, et al., "Use of a Novel 5'-Regioselective Phosphitylating Reagent for One-Pot Synthesis of Nucleoside 5'-Triphosphates from Unprotected Nucleosides," *Current Protocols in Nucleic Acid Chemistry*, 2013, 1.30.1-1.30.21; Nagata S, et al., "Improved method for the solid-phase synthesis of oligoribonucleotide 5'-triphosphates," *Chem. Pharm. Bull.*, 2012, 60(9):1212-15; Abramova et al., "A facile and effective synthesis of dinucleotide 5' triphosphates," *Bioorg. Med. Chem.*, 15:6549-6555, 2007; Abramova et al., "Synthesis of morpholine nucleoside triphosphates," *Tet. Lett.*, 45:4361, 2004; Lebedev et al., "Preparation of oligodeoxyribonucleotide 5'-triphosphates using solid support approach," *Nucleos. Nucleot. Nucleic. Acids*, 20: 1403, 2001; Hamel et al., "Synthesis of deoxyguanosine polyphosphates and their interactions with the guanosine 5'-triphosphate requiring protein synthetic enzymes of *Escherichia coli*," *Biochemistry*, 1975, 14(23):5055-5060; Vaghefi M., "Chemical synthesis of nucleoside 5'-triphosphates," In: Nucleoside Triphosphates and their Analogs, pp. 1-22, Taylor & Francis, 2005; Burgess et al., "Synthesis of nucleoside triphosphates," *Chem. Rev.*, 100:2047-2059, 2000). One such method that is commonly used is illustrated in Scheme IV:

Scheme IV

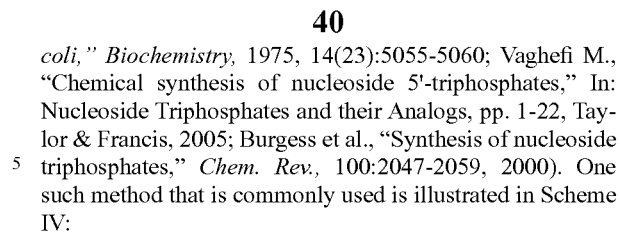

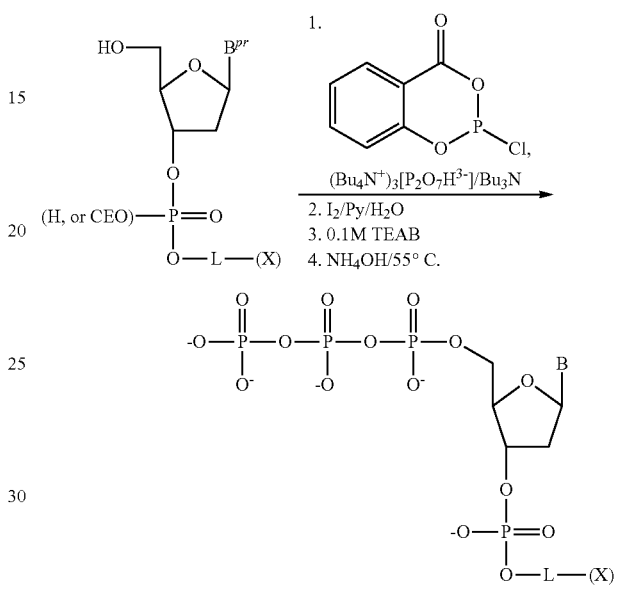

Finally, a detection group may be added to the end of the linker after deprotecting the reactive functional group "X", as depicted in Scheme V. Here, the variable reactive groups "X" on the linker, and "Y" on the detection group, react together to form the linkage "Q", as defined above.

Scheme V

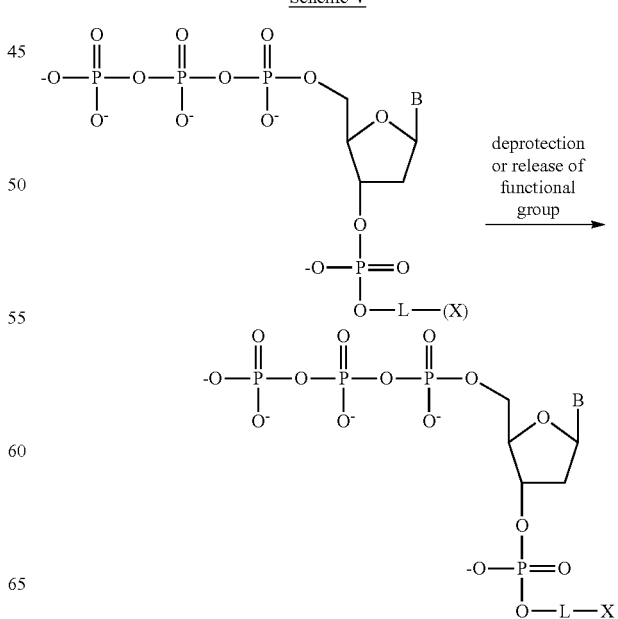

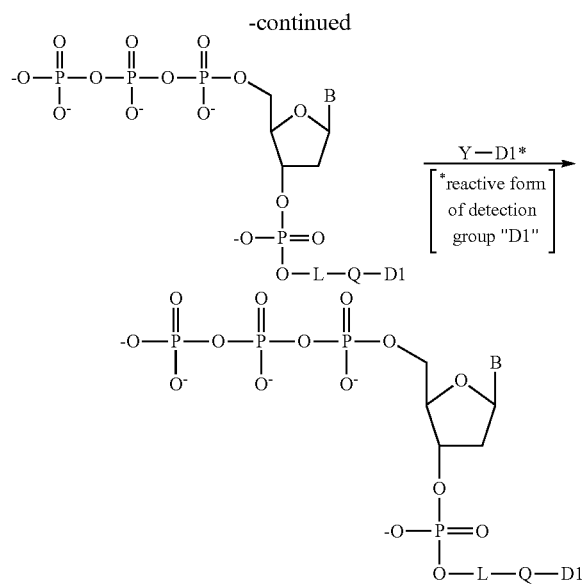

The synthesis described in Scheme VI (below) further illustrates how these methodologies are employed to prepare a deoxynucleotide 5'-triphosphate which has a 4-chlorophenyl phosphate blocking group to which an azide-functionalized alkynyl-poly(ethylene glycol) linker is attached. The resulting azido modified-nucleoside tetraphosphate can be coupled to an alkynyl-modified fluorescent dye, eg., those commercially available from Jena Biosciences, Inc., Jena, Germany, in the presence of a Cu(I) catalyst using Huisgen "click chemistry". (See, El-Sagheer et al., "Click Chemistry with DNA," *Chem. Soc. Rev.*, 2010, 39: 1388-1405, and Amblard et al., "Cu(I)-Catalyzed Huisgen Azide-Alkyne 1,3-Dipolar Cycloaddition Reaction in Nucleoside, Nucleotide, and Oligonucleotide Chemistry," *Chem. Rev.*, 2009, 109(9): 4207-4220). Alternatively (as is shown, below), the azide may be reduced to a primary amine, using a reagent such as tris(carboxyethyl)phosphine (TCEP), and then reacted any fluorescent dye NHS ester derivative, which are available from commercial sources (Life Technologies, Inc., Grand Island, N.Y.; ATTO-TEC GmbH, Siegen, Germany; and Jena Biosciences, Inc., Jena, Germany, etc.).

Scheme VI

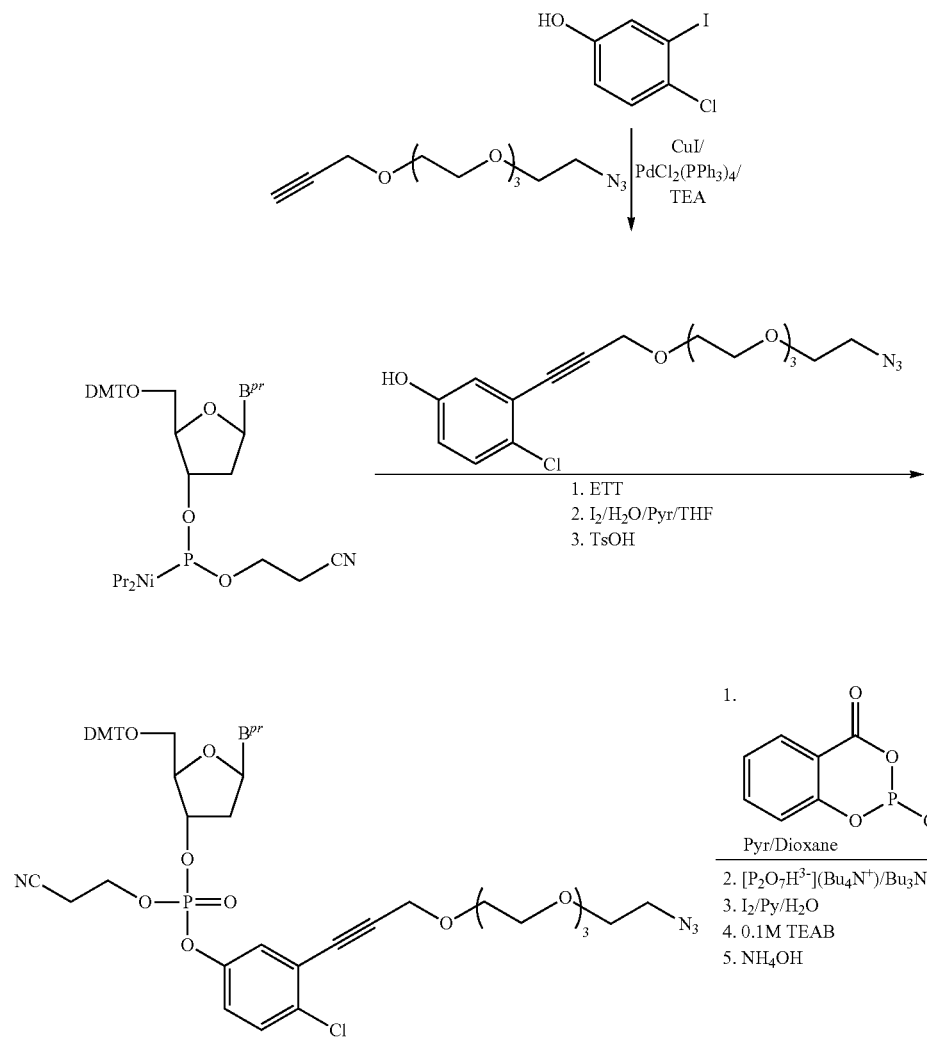

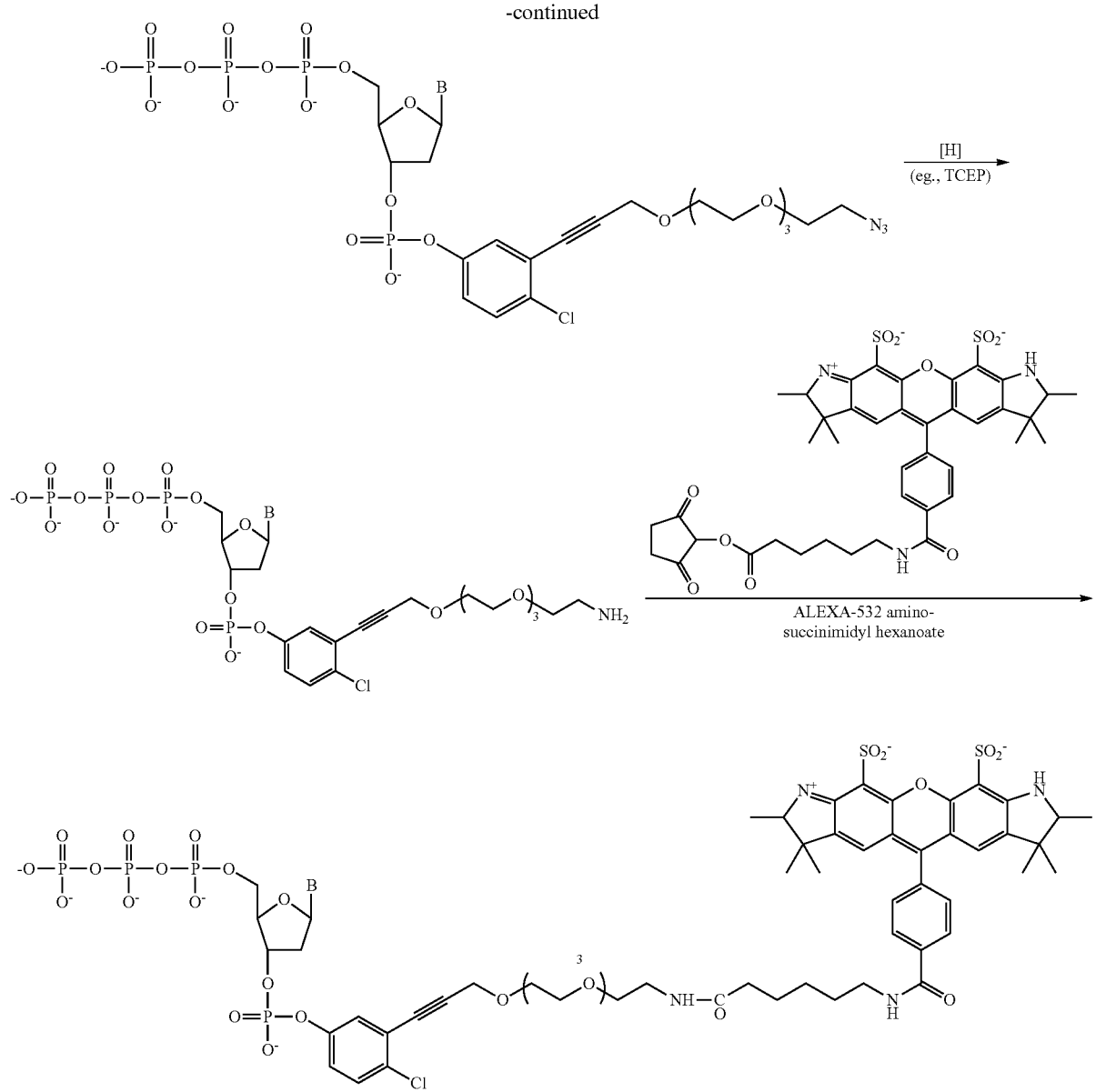
Example 1
Synthesis of $N^4$-acetyl-3'(O-4-chlorophenyl-O'-3-cyanoethyl)-phosphate-2'deoxy-cytidine-5'-triphosphate (3'-CCP-dCTP, 1) follows Scheme VII, below, where in this example, $B^{pr}$ represents an $N^4$-acetyl-protected cytidine base ($C^{Ac}$), but the same procedure may be followed for any protected nucleotide.
Scheme VII
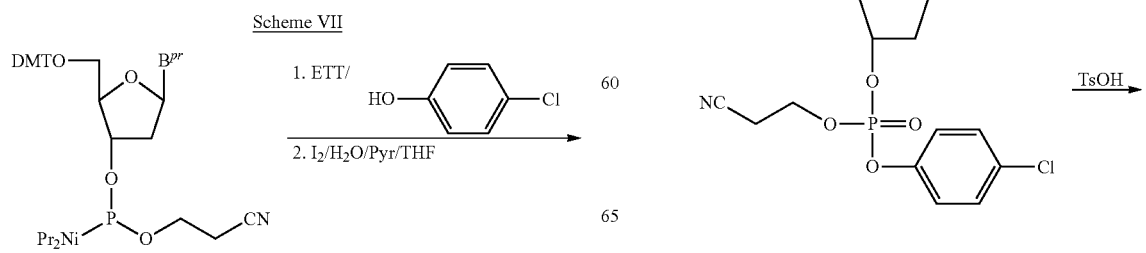

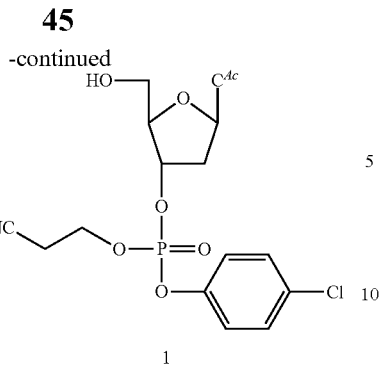

1

To a solution of 5'-dimethoxytrityl-N-acetyl-2'-deoxycytidine,3'-[(2-cyanoethyl)-(N,N-diisopropyl)]-phosphoramidite in anhydrous acetonitrile (2.0 g in 26 mL, 2.6 mmol) was added 5-(ethylthio)tetrazole (0.25 M solution, 23 mL, 5.75 mmol) under argon, and this was followed by addition of a solution of 4-chlorophenol (0.46 g, 2.2 mmol.) in 20.0 mL anhydrous acetonitrile. After stirring for 1 h at room temperature, the solution was cooled to 4° C., and 30 mL of iodine solution (0.1 M in THF/pyridine/$H_2O$-78:20:2) was added and reaction was stirred for an additional 30 minutes at room temperature and then diluted with 150 mL of ethyl acetate and washed with saturated aqueous sodium thiosulfate.

The organic layer was then washed with brine, dried over anhydrous sodium sulfate and concentrated to afford a pale yellow oil. The crude product was dissolved in dichloromethane (200 mL). p-Toluenesulfonic acid (0.5 g, 2.6 mmol) was added, and the solution was stirred for 20 min (TLC shows no starting material). The solution was then washed with saturated aqueous sodium bicarbonate, dried with sodium sulfate, and concentrated under vacuum. The resulting crude product (an oil) was purified by flash chromatography (5 to 10% methanol in ethyl acetate) and the desired product isolated as white solid (0.82 g, 62%). $^1$H-NMR (300 MHz, $CDCl_3$) δ 8.20 (d, J=7.5 Hz, 1H), 7.44, (d, J=7.5 Hz, 1H), 7.35 (d, J=8.7 Hz, 2H), 7.18 (d, J=8.7 Hz, 2H), 5.36 (m, 1H), 4.35 (m, 2H), 3.90 (m, 3H), 2.83 (m, 1H), 2.54 (m, 1H), 2.24 9s, 3H). (See, Gough et al., *Nuc. Acids Res.*, 1979, 7(7): 1955-1964; and *Biochemistry*, 1980, 19(20): 4688).

Example 2

Synthesis of 3'-(O-4-chlorophenylphosphoryl)-2'-deoxy-5'-cytidine triphosphate (3'-CPP-dCTP, 2), proceeded as provided in Scheme VIII, below (where $C^{Ac}$ represents an $N^4$-acetyl-protected cytidine base):

Scheme VIII

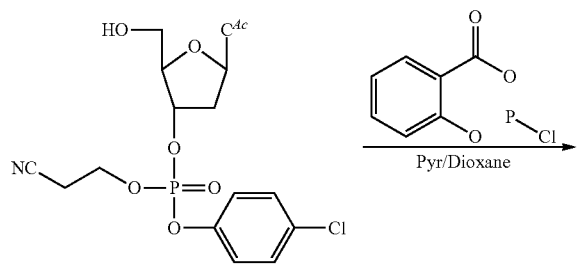

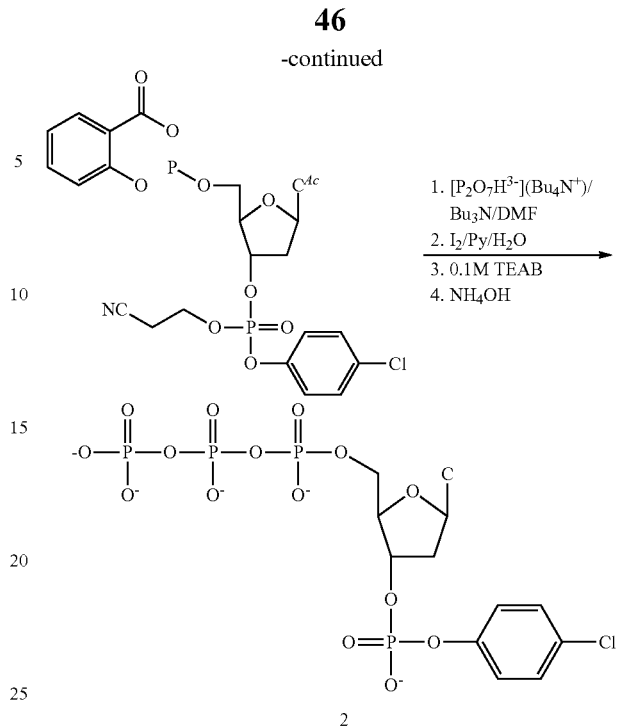

2

Anhydrous tributylamine (1.16 g, 6.3 mmol) was added through septum to a solution of tributylammonium pyrophosphate (0.55 g, 1.0 mmol) in anhydrous DMF (2.0 mL) under argon and the mixture was added slowly to a solution of 2-chloro-4-H-1,3,2-benzodioxaphosphorin-4-one (0.20 g, 1.0 mmol) in anhydrous DMF (1.5 mL). The reaction was stirred for 1 hr under argon, and the reaction mixture was then added to a solution of nucleoside from Example 1 (0.25 g, 0.5 mmol) in anhydrous DMF (5.0 mL). After stirring under argon for another 2 hr, 10 mL of iodine solution (0.2 M in THF/pyridine/$H_2O$, 78:20:2) was added. After another hour stirring, an aqueous solution of 0.1 M triethylammonium bicarbonate (20 mL) was added. Stirring was continued for 2 more hours and then the reaction mixture was concentrated under vacuum and the crude material was taken up in 20 mL of 30% aqueous ammonium hydroxide and heated for 4 h at 55° C. in a sealed pressure tube. After cooling to room temperature, the solution was evaporated to afford the crude product as a viscous oil.

Liquid chromatography/mass spectrometry (LC/MS) analysis of the crude mixture showed three main components, including the desired product (28%). The mass spectrum data of this peak at 11.1 min shows m/z 655.9 (M-H), corresponding to the calculated mass for final target product 2, 3'-CCP-dCTP (m/z 656.9).

The crude product was purified by reverse phase HPLC using a Phenomenex Luna C-18 column (5 μm, 100 Å, 150×4.6 mm) from. The desired product was eluted using TEAB in acetonitrile (ACN) with a gradient of 0-5 min (1-5% ACN), 5-18 min (5-10% ACN), 18-25 min (10-20% ACN), 25-26 min (20-1% ACN), 26-30 min (1% ACN) at a flow rate of 1 mL/min, and monitoring at 260 nm. The pooled fractions were combined, concentrated under vacuum and lyophilized to afford the product as white solid. The purity of the final product was 97.5% by analytical LC-MS.

Example 3

Primer Extension with the Reversible Terminator 3"-CPP-dCTP by EDP Polymerase, and Subsequent De-Blocking.

Primer extension was carried out using 3'-CPP-dCTP catalyzed by the enhanced DNA polymerase ("EDP"). (See, FIG. 2, lanes 3-5). Blocking of further extension after terminator incorporation is observed in a "runoff" reaction with Bst polymerase and all four unmodified dNTPs, resolved in lane 4 of FIG. 2. De-blocking was accomplished by incubation with Endonuclease IV as indicated by extension in a "runoff" reaction with Bst polymerase and all four unmodified dNTPs. (See, FIG. 2, lane 5).

Procedure: 8 nmoles of 5'-biotinylated template oligonucleotide (5'-Biotin-CTGAACGGTAGCATCTTGACGA-GATCGGAAGAGCGTCGTGTAGGGAAAGAGTGTTT CAG-3') (SEQ ID NO: 1) was immobilized on 200 μl of T1 MYONE™ streptavidin coated beads (Invitrogen/Life Technologies, Grand Island, N.Y.) by incubating in 10 mM Tris at pH 7.5 with 1M NaCl and 1 mM EDTA for 1 hour at room temperature. The beads were first washed with 1×SSC with 0.1% SDS at room temperature for 10 minutes then they were further washed three times for 10 minutes with 0.1× SSC and 0.1% SDS at 65° C. After washing, sequencing primer (2.5 nmole, 5'-ACACTCTTTCCCTACAC-GACGCTCTTCCGATCT-3') (SEQ ID NO: 2) was annealed to half of the bead stock in Bead Wash Buffer (1M NaCl, 25 mM Tris at pH 7.5, 0.01% Tween-20) in a PCR machine (program: 5 minutes at 70° C., 15 minutes at 55° C., 5 minutes at 25° C.) and washed three times with Bead Wash Buffer.

Each reaction was performed in a single tube and then split amongst the successive reactions (or gel lanes) in a manner to ensure that after all steps were complete, each gel lane contained an equal amount of anneal template. The immobilized primer-template duplex was incubated in Incorporation Buffer (Illumina, Inc., San Diego, Calif.) containing 15% (v/v) EDP at 55° C. for 1 min. The extension was initiated by adding dCTP-3'-PCPP to a final concentration of 200 μM. After another 10 minutes the extension reaction was stopped by adding an equal volume of Bead Wash Buffer and the reaction placed onto a magnetic tube rack to separate the primer-template from the reaction buffer.

The deblocking reaction was carried out by washing once with Bead Wash Buffer and incubating in 100 ul of 1×NEB Buffer 3 with 1 U/μl Endonuclease IV (NEB) for 10 min at 37° C. Runoff reactions were performed in 50 μl of 1× Thermopol buffer (NEB) with 1.6 U/μl of Bst Polymerase, 4 mM DTT, 1 mg/mL BSA, 0.2 mg/mL PVP-10, and 100 μM nucleotides (dNTP). dCTP was incorporated in 1× Thermopol buffer (NEB) with 1.6 U/μl of Bst Polymerase, 4 mM DTT, 1 mg/mL BSA, 0.2 mg/mL PVP-10, and 10 μM dCTP for 2 minutes at 37° C. Sequencing primer for all reactions was eluted from the beads by incubating with 10 ul of 0.1N NaOH, for 10 min at room temperature and added to 11.5 μl of 2×TBE-Urea loading buffer with 1.5 μl of 1M Tris (pH 8.0) and denatured at 70° C. for 3 minutes before being run on a 15% TBE-Urea acrylamide gel.

Figure 2:
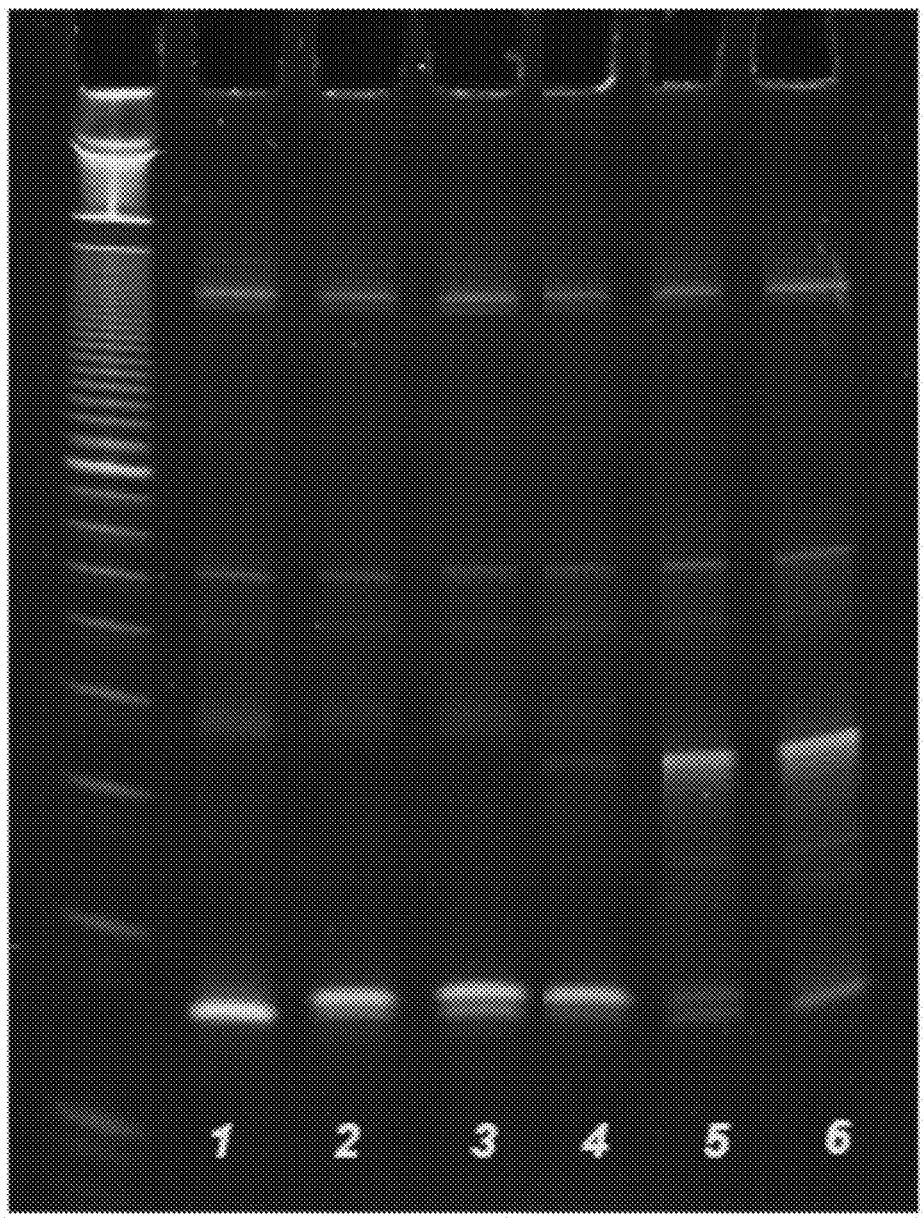
FIG. 2: Primer extension with the reversible terminator 3'-CPP-dCTP by EDP polymerase, and subsequent de-blocking.

In FIG. 2, the first unnumbered lane is a control DNA size ladder where the bottom-most band corresponds to 30 bp and the next higher band corresponds to 40 bp. The results are shown in lanes 1-6 of FIG. 2, and are as follows:
(1) unmodified 33-mer primer (negative control) provides background signal
(2) primer extended with dCTP and Bst polymerase conducted at 55° C., for 5 minutes—this experiment shows the expected appearance of a new, slower band slightly higher than the 33-mer primer seen in lane 1, corresponding to a single-nucleotide addition product
(3) primer extension with dCTP-3'-PCPP using EDP polymerase conducted at 55° C., for 10 minutes—this experiment shows the appearance of a new, slower band slightly above the band in lane 2, corresponding to a single-nucleotide addition product similar to that observed using dCTP
(4) Reaction includes primer extension with dCTP-3'-PCPP using EDP polymerase at 55° C., 10 minutes; followed by a runoff extension reaction with Bst and all four deoxyribonucleotides conducted at 55° C., for 5 minutes—this experiment shows that the single-nucleotide extension product produced with dCTP-3'-PCPP remains blocked and unextended because no additional bands appear above the band running parallel with the band observed in lane 3
(5) Reaction includes primer extension with dCTP-3'-PCPP using EDP polymerase conducted at 55° C., for 10 minutes; followed by Endonuclease IV treatment performed at 37° C., for 10 minutes; and then by a runoff reaction with Bst and all four deoxyribonucleotides for 5 minutes at 55° C.—this experiment shows that Endonuclease IV released the blockage, thereby allowing runoff extension (polymerization by Bst polymerase) to proceed unhindered, yielding a larger species indicated by the much slower moving band well above the band observed in lanes 3 and 4, and running parallel with the band observed in the positive control (lane 6)
(6) unmodified 33-mer primer in a runoff extension reaction (positive control)

Example 4

The following examples are provided to show that dCTP-3'-PCPP is also incorporated into a growing DNA chain using THERMINATORT™ III.

Procedure: Template and primer DNA sequences are as provided in Example 3. As above, template DNA was immobilized on T1 MyOne streptavidin coated beads and a sequencing primer was annealed after washing. Immobilized primer-template was incubated in 50 μl of 1× Thermopol Buffer (NEB) with 0.4 U/μl of THERMINATOR™ III and 4 mM MnCl$_2$ spiked-in at 65° C. for 1 min. The reaction was initiated by adding 200 μM 3'-CPP-dCTP. After 10 minutes the extension was stopped by adding an equal volume of Bead Wash Buffer (1M NaCl, 25 mM Tris at pH 7.5, 0.01% Tween-20) and placing the reaction onto a magnetic tube rack to separate the primed template from the reaction buffer. The reaction was washed with Bead Wash Buffer and runoff reactions were performed in 50 μl of 1× Thermopol buffer with 4 mM DTT, 1 mg/mL BSA, 0.2 mg/mL PVP-10, and nucleotides (100 μM dNTP), with 1.6 U/μl of Bst Polymerase. dCTP was incorporated in 1× Thermopol buffer (NEB) with 1.6 U/μl of Bst Polymerase, 4 mM DTT, 1 mg/mL BSA, 0.2 mg/mL PVP-10, and 10 μM dCTP for 2 minutes at 37° C. Sequencing primer for all reactions was stripped in 0.1N NaOH, added to TBE-Urea loading buffer with 1M Tris (pH 8.0) and denatured at 70° C. for 3 minutes before being run on a 15% TBE-Urea acrylamide gel as above. (See, FIG. 3).

Figure 3:
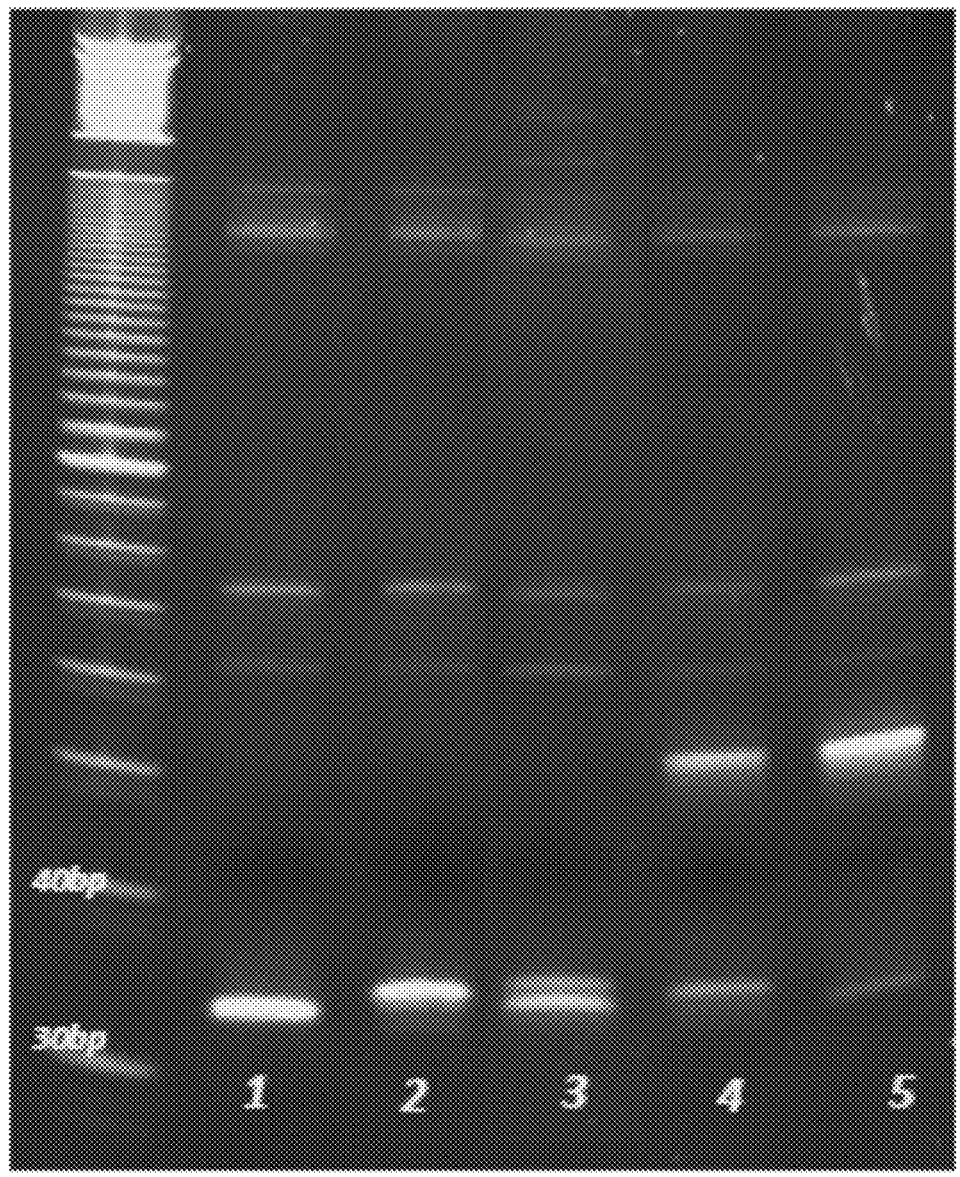
FIG. 3: Primer extension with the reversible terminator dCTP-3'-PCPP into a growing DNA chain using THERMINATOR™ III, and subsequent de-blocking.

In FIG. 3, the first unnumbered lane is a control DNA size ladder where the bottom-most band corresponds to 30 bp and the next higher band corresponds to 40 bp. The results are shown in lanes 1-6 of FIG. 2, and are as follows:
(1) unmodified 33-mer primer (negative control)
(2) primer extended with dCTP and Bst polymerase conducted at 55° C. for 5 minutes—this experiment shows the expected appearance of a new, slower band corresponding to a single-nucleotide addition product, migrating slightly higher than the control band in lane 1 which is unmodified 33-mer primer
(3) primer extension with dCTP-3'-PCPP using THERMINATOR™ III polymerase conducted at 55° C. for 10 minutes in buffer including 4 mM MnCl$_2$—this experiment shows the appearance of a new, slower band migrating slightly higher than the band in lane 2, corresponding to a single-nucleotide addition product similar to that observed using dCTP; it is apparent that this reaction is inefficient, and only partial extension is observed (4) primer extension with dCTP-3'-PCPP using THERMINATOR™ III polymerase conducted at 55° C. for 10 minutes in buffer including 4 mM MnCl$_2$; followed by a runoff extension reaction with Bst and all four deoxyribonucleotides conducted at 55° C. for 5 minutes—this experiment shows that the single-nucleotide extension product produced with dCTP-3'-PCPP remains blocked and unextended (5) unmodified 33-mer primer in a runoff extension reaction conducted at 55° C. for 5 minutes using 100 μM Bst polymerase in the presence of dNTP (positive control).

What is claimed is:

1. A reversible terminator compound selected from the group consisting of Formula:

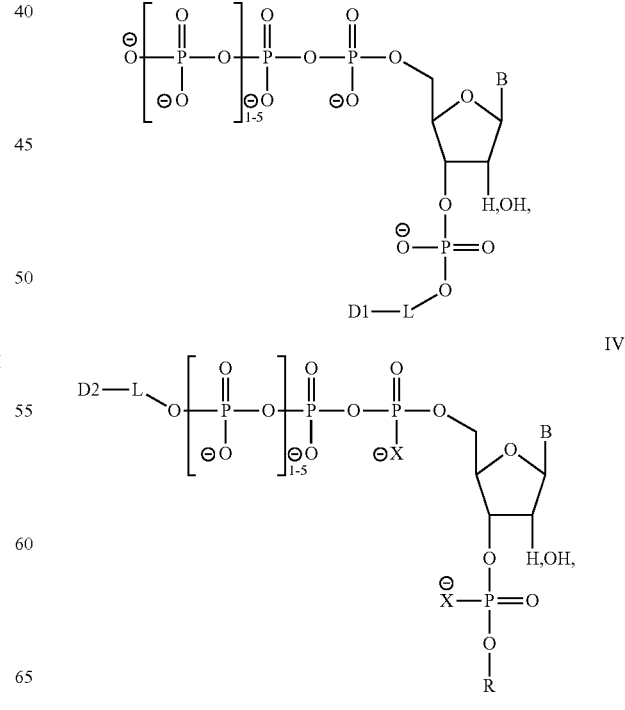

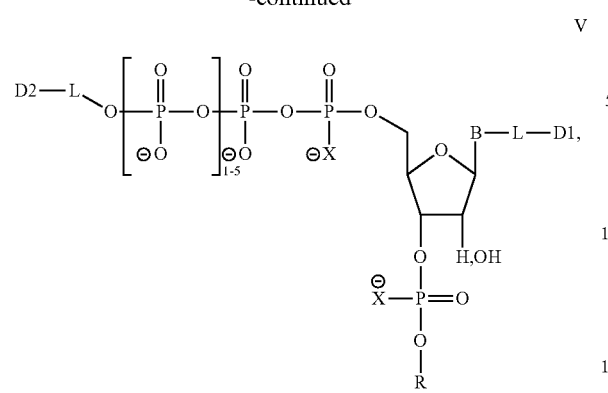
V
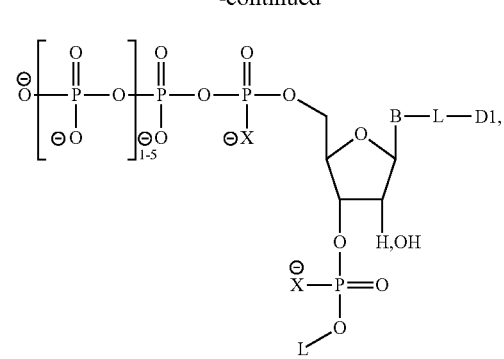
IX
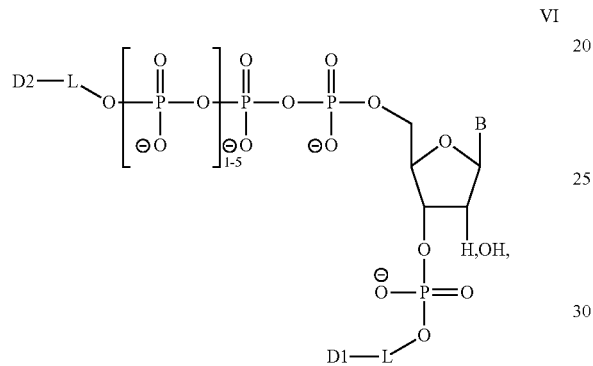
VI
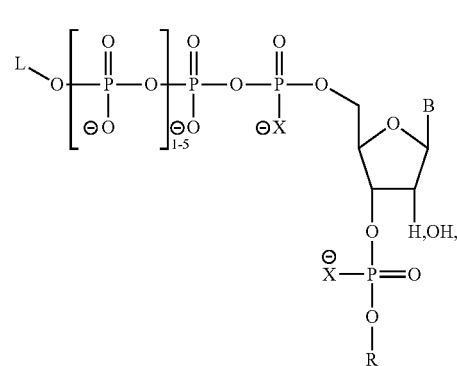
X
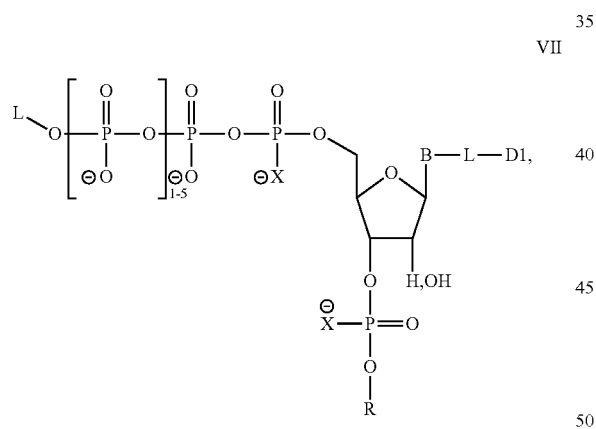
VII
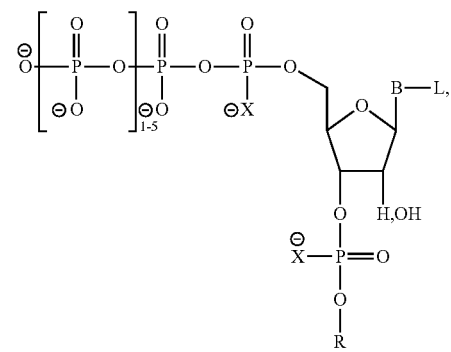
XI
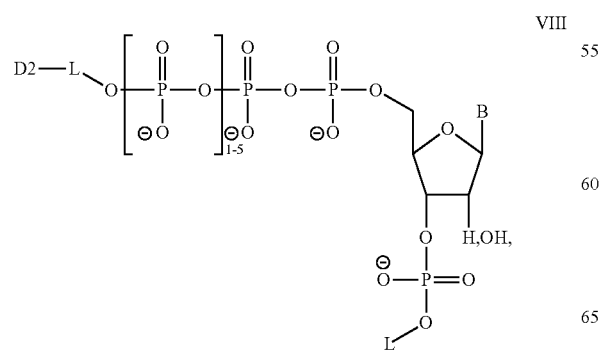
VIII
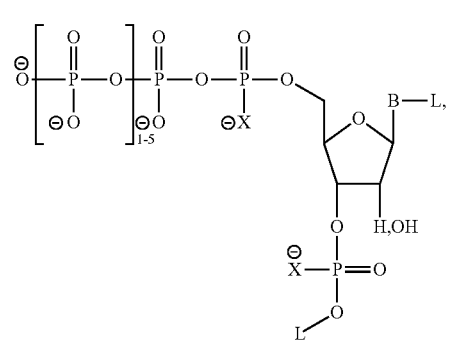
XII -continued

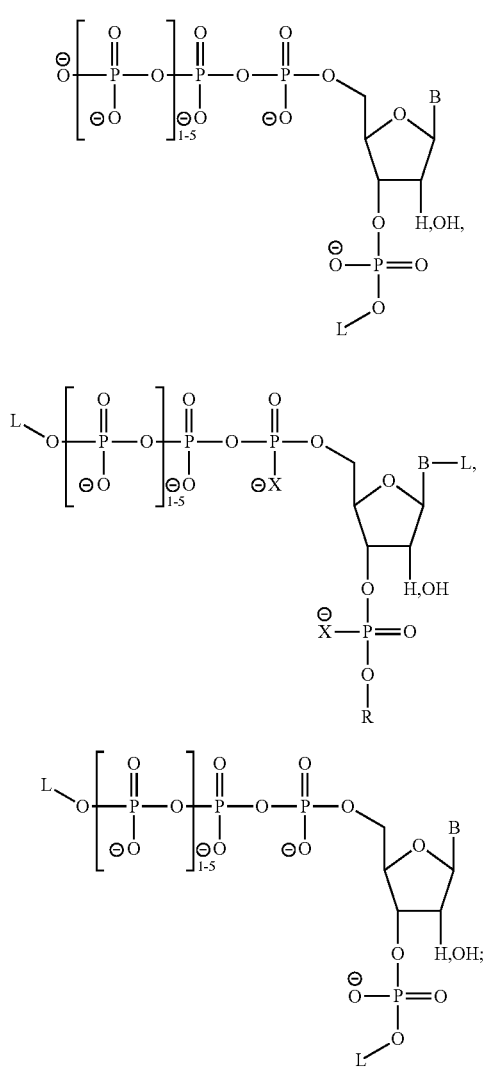

wherein:
R is a $C_1$-$C_6$ alkyl that is optionally substituted or an aryl group that is optionally substituted,
X is O, S, or $BH_3$,
B is a heterocyclic nucleic acid base that is optionally substituted, or an analog thereof,
L is a linker group which is optionally cleavable, wherein L groups are the same or different, and
D1 and D2 are detectable labels,
wherein at least one linker group is selected from the group consisting of:
*—$(CH_2)_6$—NHC(O)$(CH_2)_n$—NHC(O)—,
*—$CH_2(CH_2OCH_2)_3CH_2$—NHC(O)—$(CH_2)_n$—NHC(O)—,
*—$CH_2CH(CH_2CH_2OH)(OCH_2CH_2)_m$—NHC(O)—$(CH_2)_n$—NHC(O)—,

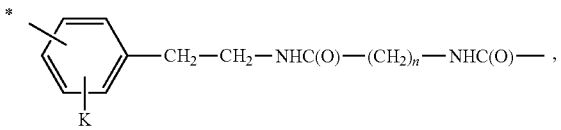

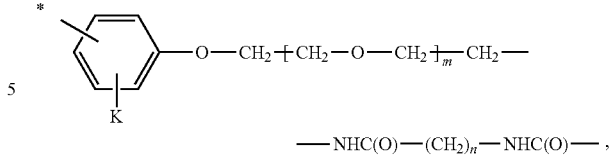

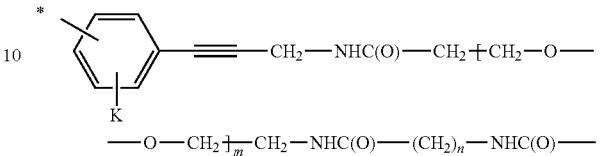

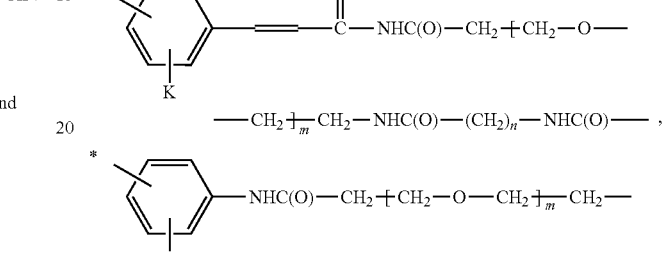

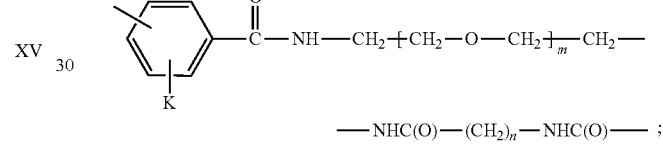

wherein:
K is an optional substituent or functional group,
n is an integer from 2 to 10,
m is an integer from 0 to 18, and
the linker group is bound to a nucleotide through the * end.

2. The compound according to claim 1, wherein B is selected from the group consisting of naturally occurring guanine, cytosine, adenine, uracil and thymine.

3. The compound according to claim 1, wherein R is chlorophenyl that is optionally substituted.

4. The compound according to claim 1, wherein R is selected from the group consisting of methyl, ethyl, propyl, butyl, pentyl and hexyl.

5. The compound according to claim 1, wherein K is a halogen.

6. The compound according to claim 1, wherein D1 and/or D2 are fluorescent detectable labels.

7. The compound according to claim 1, wherein D1 and D2 are acceptor-donor FRET pair labels.

8. A composition, comprising two or more reversible terminators of claim 1, wherein each reversible terminator associated with each base B is individually attached to a different fluorescent label such that each base B is detectably distinguishable from any other different base B.

9. A nucleotide comprising:
a sugar moiety covalently bound at a 3-oxygen to a phosphate moiety, wherein the atoms at the bonding positions are oxygen, and an atom or group at a non-bonding position of the phosphate moiety is selected from an oxygen atom, a sulfur atom or a $BH_3$ group; and a removable blocking group bound to the phosphate moiety,
wherein the blocking group further comprises a linker group, and
wherein the linker group is selected from the group consisting of:

*—$(CH_2)_6$—NHC(O)$(CH_2)_n$—NHC(O)—,
*—$CH_2(CH_2OCH_2)_3CH_2$—NHC(O)—$(CH_2)_n$—NHC(O)—,
*—$CH_2CH(CH_2CH_2OH)(OCH_2CH_2)_m$—NHC(O)—$(CH_2)_n$—NHC(O)—,

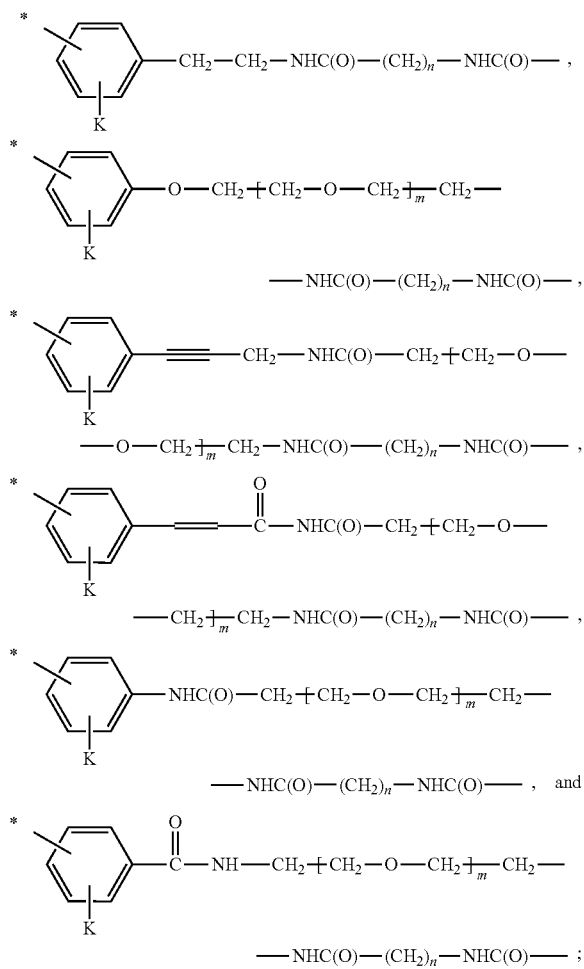

wherein:
K is an optional substituent or functional group,
n is an integer from 2 to 10,
m is an integer from 0 to 18, and
the linker group is bound to the blocking group through the * end and optionally to a label at the other end.

10. The nucleotide according to claim 9, wherein the nucleotide has covalently attached to the 5' hydroxyl group one or more phosphate groups.

11. The nucleotide according to claim 10, wherein the 5' hydroxyl group has covalently attached thereto three or five phosphate groups.

12. The nucleotide according to claim 9, wherein the blocking group is removable by incubation with one or more enzymes.

13. The nucleotide according to claim 12, where the one or more enzymes are selected from the group consisting of: phosphodiesterase and phospholipase.

14. The nucleotide according to claim 12, wherein the enzyme is endonuclease IV.

15. The nucleotide according to claim 9, wherein the label is present and the label is a fluorescent dye.

16. The nucleotide according to claim 9, where the base is selected from the group consisting of naturally occurring: C, A, T, and G.

17. A composition, comprising two or more nucleotides of claim 16, wherein each different nucleotide of claim 16 comprising a different base comprises a blocking group comprising a label, and wherein each label is different allowing differential detection of each of C, A, T, and G.

18. The nucleotide according to claim 9, wherein a 2' position the sugar moiety has covalently attached thereto a hydroxyl group.

19. A reversible terminator compound selected from the group consisting of Formula:

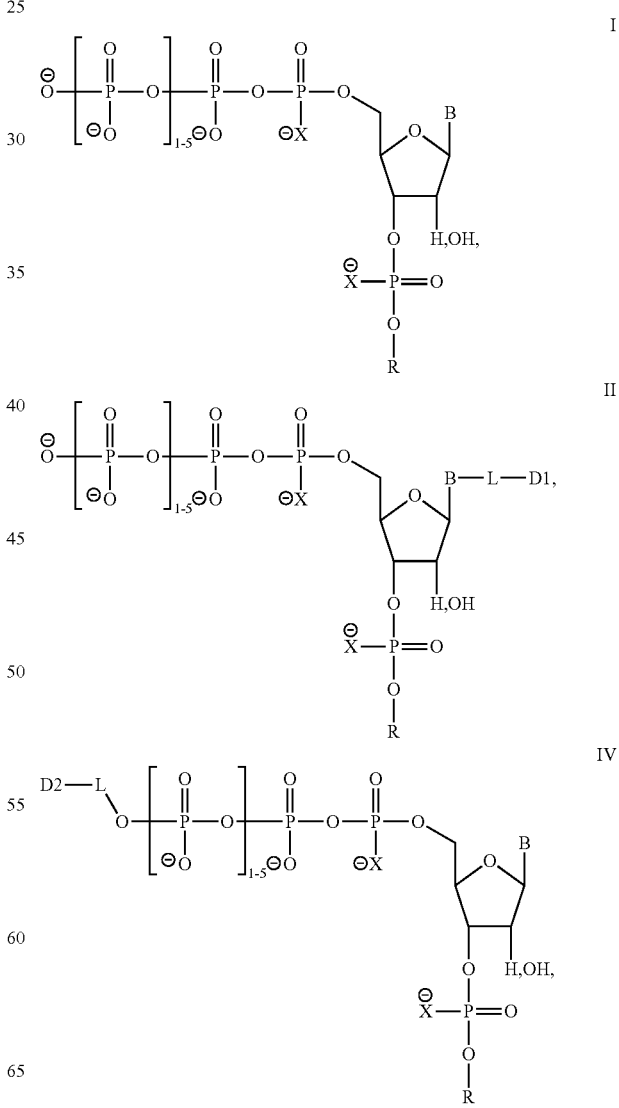

V

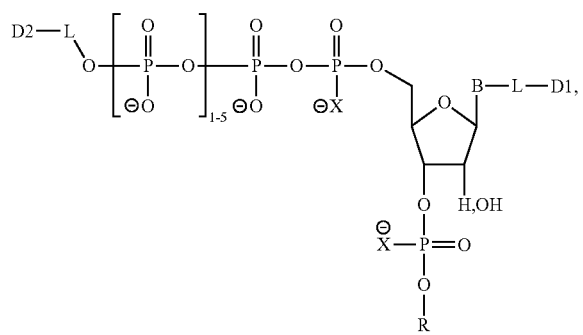

VII

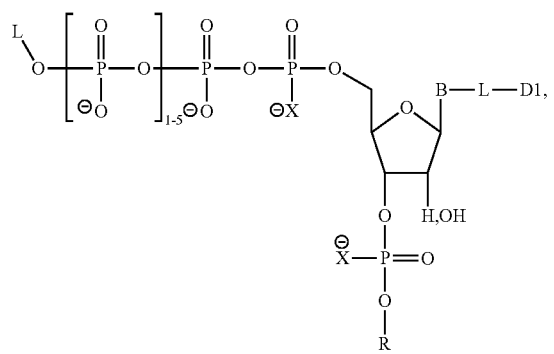

X

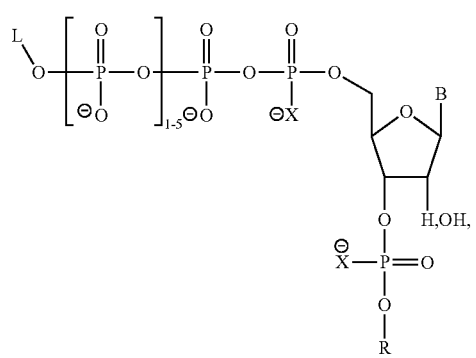

XI

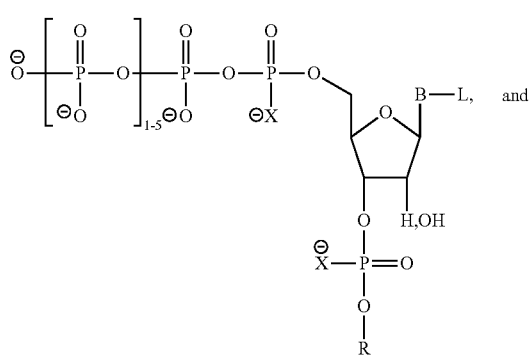

XIV

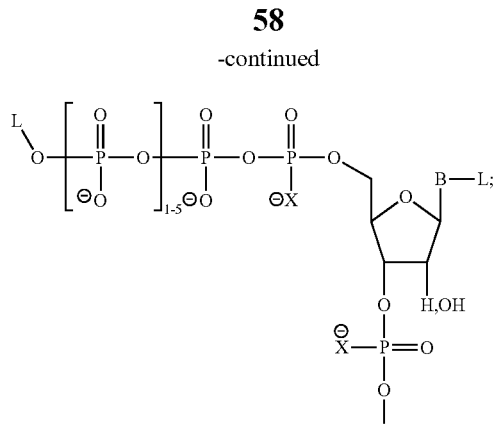

wherein:

X is O, S, or $BH_3$,

B is a heterocyclic nucleic acid base that is optionally substituted, or an analog thereof, L is a linker group which is optionally cleavable, wherein L groups are the same or different, D1 and D2 are detectable labels, and R is chlorophenyl that is optionally substituted.

20. The compound according to claim 19, wherein:

the compound is Formula (II), and

R has the structure

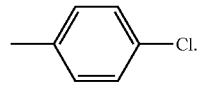

21. The compound according to claim 20, wherein:

X is O, and the variable number of phosphates is 1.

22. A reversible terminator compound selected from the group consisting of Formula:

II

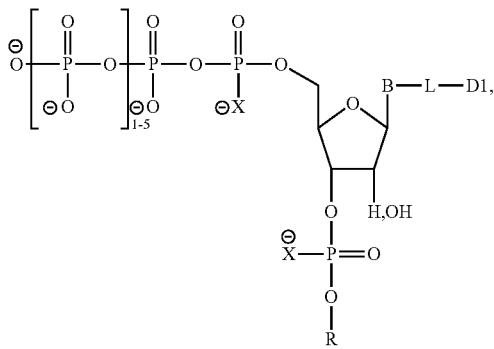

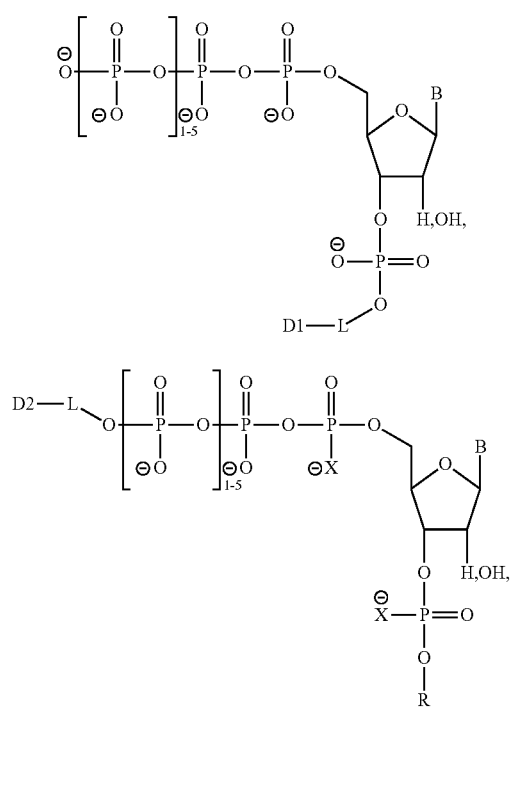
III
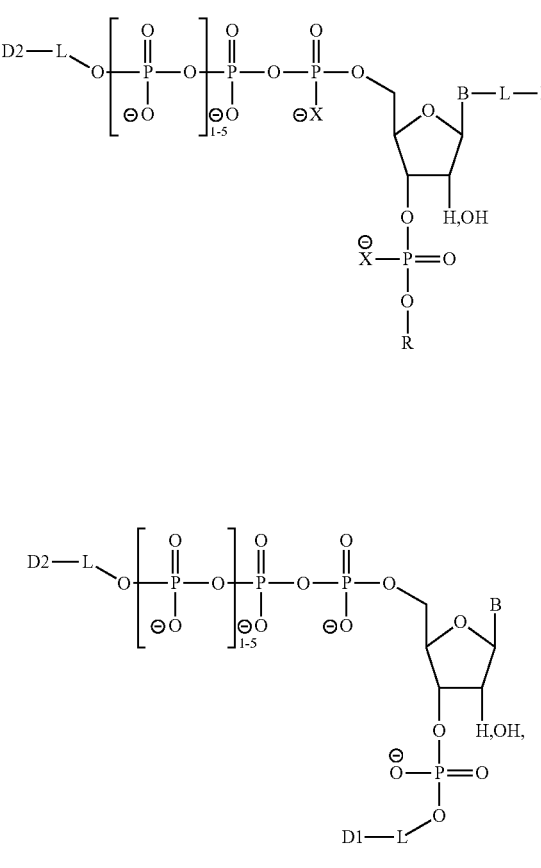
IV
V
VI
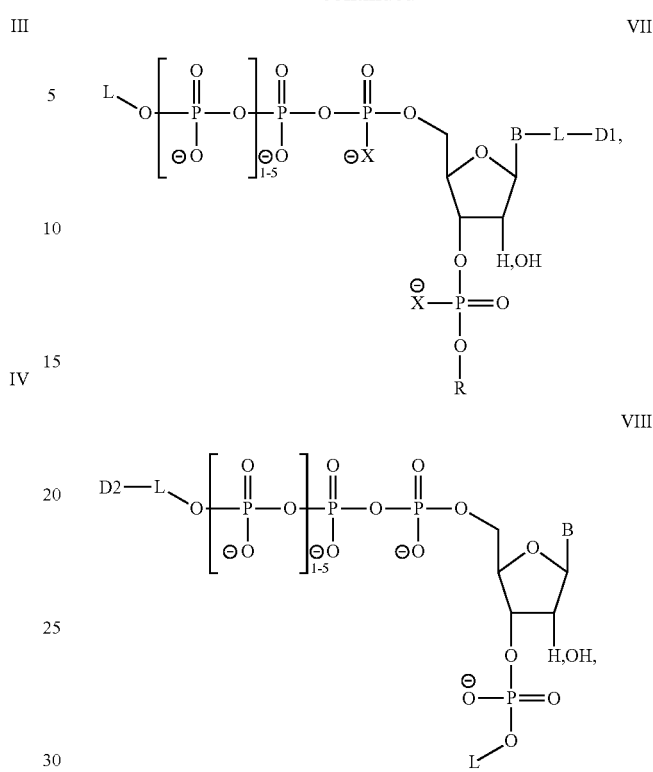
VII
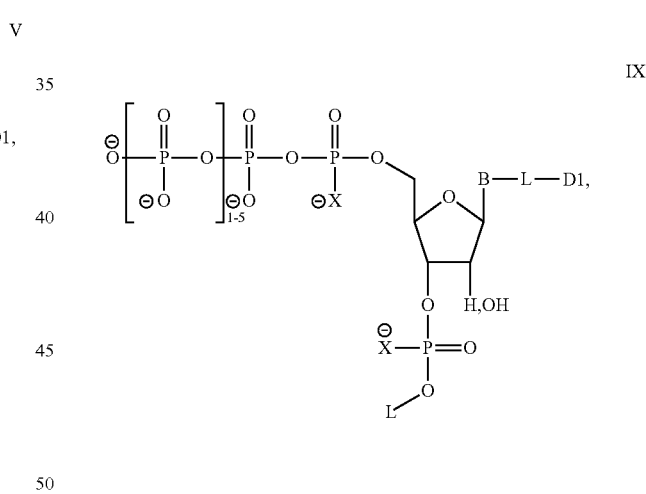
VIII
IX
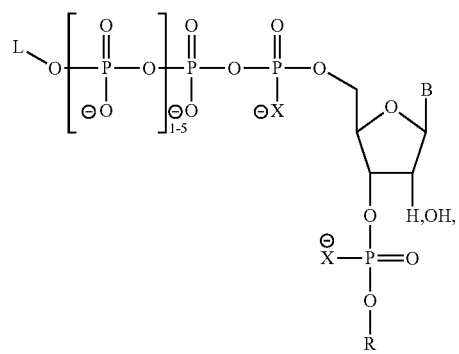
X

XI

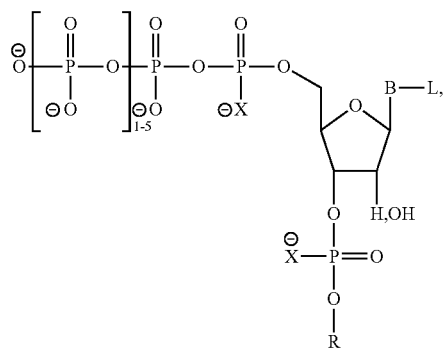

XII

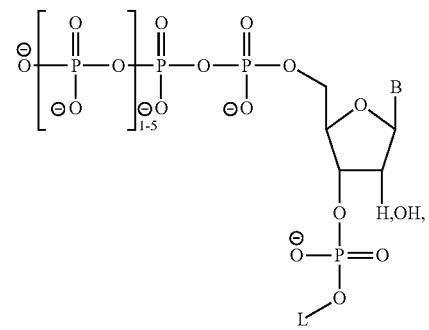

XIII

XIV

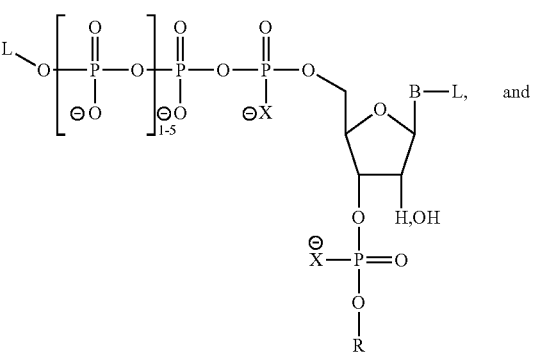 and

XV

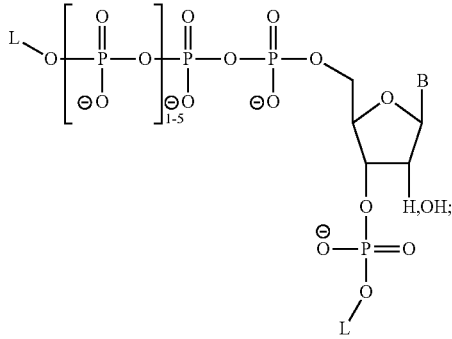

wherein:

R is a $C_1$-$C_6$ alkyl that is optionally substituted or an aryl group that is optionally substituted, X is O, S, or $BH_3$, B is a heterocyclic nucleic acid base that is optionally substituted, or an analog thereof, D1 and D2 are detectable labels, and L is a linker group which is optionally cleavable, wherein L groups are the same or different, wherein:

linker L has the structure depicted in Scheme I:

Scheme I

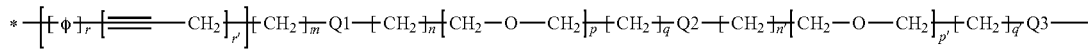

wherein:
m is an integer from 0 to 9,
r and r' are independently either 0 or 1,
  wherein at least one of r and r' is 1,
n and n' are independently either 1 or 2,
p and p' are independently integers from 0 to 18,
q and q' are independently either 1 or 2,
Φ is a cyclic alkane or alkene, an aromatic, heterocyclic or fused ring structure,
Q1-Q3 are independently optional connecting groups, and wherein:
R is

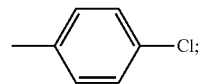

X is O;
B is a heterocyclic nucleic acid base that is optionally substituted, or an analog thereof;
L is the structure of Scheme I:

Scheme I

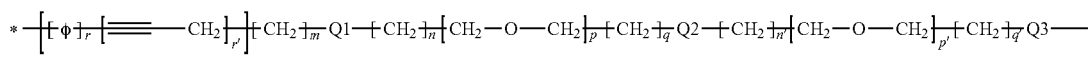

the linker group is bound to a nucleotide through the * end.

23. The compound according to claim 22, wherein Q1-Q3 are independently one or more of the following:

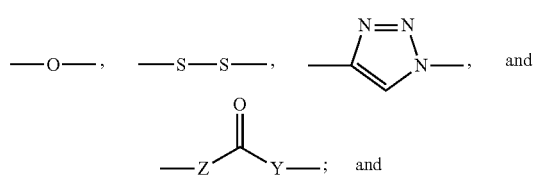

wherein Z and Y are independently optional bridging moieties selected from the group consisting of: O, S, NH, $CH_2$, —CH=CH—, and

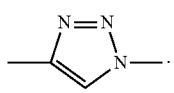

24. The compound according to claim 23, wherein:
the compound is Formula (III).
25. The compound according to claim 24, wherein:
X is O, and
the variable number of phosphates is 1.
26. A reversible terminator compound of Formula (II'):

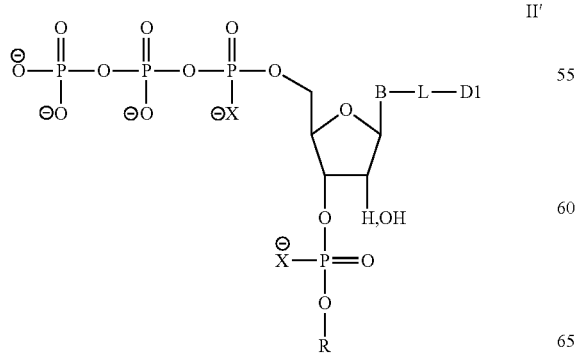

wherein:
m is an integer from 0 to 9,
r and r' are independently either 0 or 1
n and n' are independently either 1 or 2,
p and p' are independently integers from 0 to 18,
q and q' are independently either 1 or 2,
the linker is bound to the heterocyclic nucleic acid base through the * end,
Φ is a cyclic alkane or alkene, an aromatic, heterocyclic or fused ring structure, and
Q1-Q3 are independently optional connecting groups
wherein Q1-Q3 are independently one or more of the following:
—O—, —S—S—,

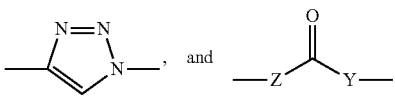

wherein Z and Y are independently optional bridging moieties selected from the group consisting of: O, S, NH, $CH_2$, —CH=CH—, and

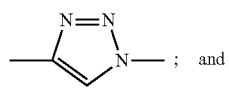

$D_1$ is a detectable label.

27. A reversible terminator compound of Formula (I-A):

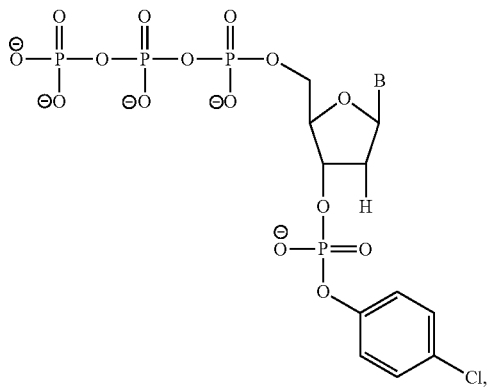

I-A wherein B is a heterocyclic nucleic acid base that is optionally substituted, or an analog thereof.

28. The compound according to claim 27, wherein B is selected from the group consisting of naturally occurring guanine, cytosine, adenine, uracil and thymine.

29. The compound according to claim 1, wherein R is the $C_1$-$C_6$ alkyl and the $C_1$-$C_6$ alkyl is optionally substituted by a substituent selected from the group consisting of —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR'—C(NR"R'")=NR"", —S(O)R', —S(O)$_2$R', —S(O)$_2$NR'R", —NRSO$_2$R', —CN and —NO$_2$;

wherein R', R", R'" and R"" are each independently selected from hydrogen, substituted or unsubstituted heteroalkyl, substituted or unsubstituted aryl, substituted or unsubstituted alkyl, alkoxy, thioalkoxy, and arylalkyl, and wherein when R' and R" are attached to the same nitrogen atom, they can be combined with the nitrogen atom to form a 5-, 6-, or 7-membered ring.

30. The compound according to claim 1, wherein R is the aryl group, and the aryl group is optionally substituted by a substituent selected from the group consisting of halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR', —C(NR'R"R'")=NR"', —NR', —C(NR"R'")=NR"", —S(O)R', —S(O)$_2$R', —S(O)$_2$ NR'R", —NRSO$_2$R', —CN and —NO$_2$, —R', —N$_3$, —CH(Ph)$_2$, fluoro($C_1$-$C_4$)alkoxy, and fluoro($C_1$-$C_4$) alkyl;

wherein R', R", R'" and R"" are each independently selected from hydrogen, substituted or unsubstituted alkyl, substituted or unsubstituted heteroalkyl, substituted or unsubstituted aryl and substituted or unsubstituted heteroaryl.

31. The compound according to claim 19, wherein B is selected from the group consisting of naturally occurring guanine, cytosine, adenine, uracil and thymine.

32. The compound according to claim 19, wherein at least one linker group L has the structure depicted in Scheme I:

Scheme I

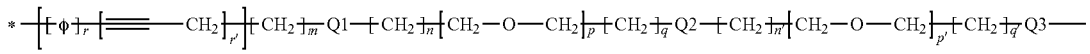

wherein:
m is an integer from 0 to 9,
r and r' are independently either 0 or 1,
n and n' are independently either 1 or 2,
p and p' are independently integers from 0 to 18,
q and q' are independently either 1 or 2,
Φ is a cyclic alkane or alkene, an aromatic, heterocyclic or fused ring structure,
Q1-Q3 are independently optional connecting groups, and the linker group is bound to a nucleotide through the * end.

33. The compound according to claim 32, wherein the at least one linker group is selected from one or more of the group consisting of:

*—(CH$_2$)$_6$—NHC(O)(CH$_2$)$_n$—NHC(O)—,
*—CH$_2$(CH$_2$OCH$_2$)$_3$CH$_2$—NHC(O)—(CH$_2$)$_n$—NHC(O)—,
*—CH$_2$CH(CH$_2$CH$_2$OH)(OCH$_2$CH$_2$)$_m$—NHC(O)—(CH$_2$)$_n$—NHC(O)—,

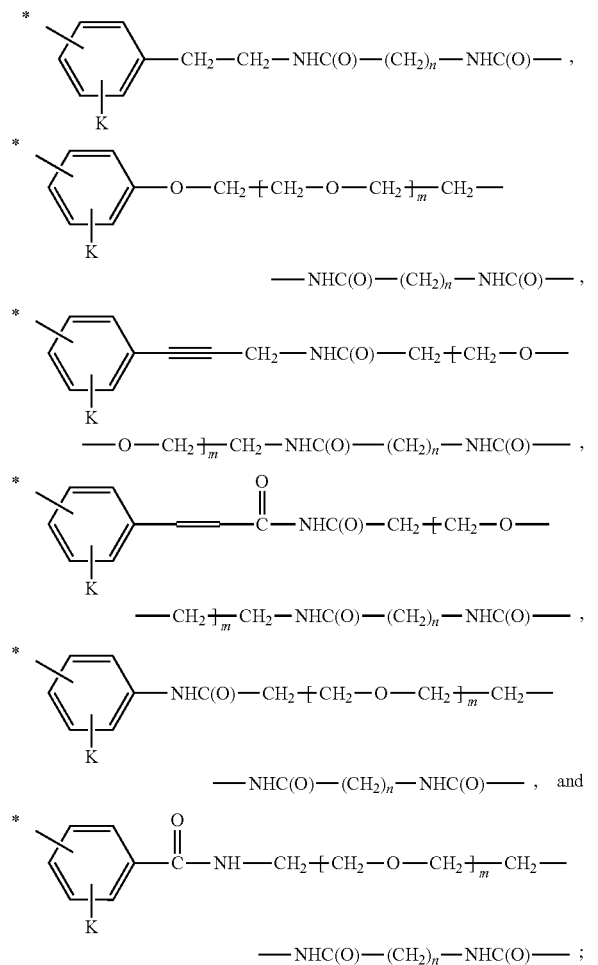

wherein:
K is an optional substituent or functional group,
n is an integer from 2 to 10,
m is an integer from 0 to 18, and
the linker group is bound to a nucleotide through the * end.

34. The compound according to claim 32, wherein Q1-Q3 are independently one or more of the following:

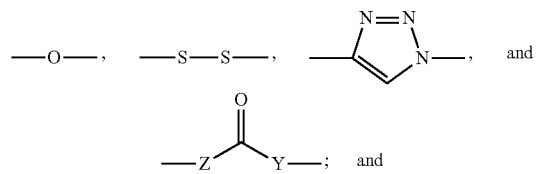

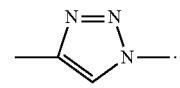

wherein Z and Y are independently optional bridging moieties selected from the group consisting of: O, S, NH, CH$_2$, —CH═CH—, and

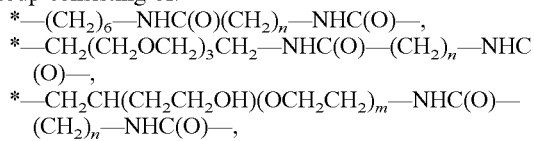

35. The compound according to claim 33, wherein K is a halogen.
36. The compound according to claim 19, wherein D1 and/or D2 are fluorescent detectable labels.
37. The compound according to claim 19, wherein D1 and D2 are acceptor-donor FRET pair labels.
38. A composition, comprising two or more nucleotides of claim 31, wherein each reversible terminator of claim 31 associated with each base B is individually attached to a different fluorescent label such that each base B is detectably distinguishable from any other different base B.
39. The compound according to claim 22, wherein D1 and/or D2 are fluorescent detectable labels.
40. The compound according to claim 22, wherein D1 and D2 are acceptor-donor FRET pair labels.
41. The compound according to claim 22, wherein B is selected from the group consisting of naturally occurring guanine, cytosine, adenine, uracil and thymine.
42. A composition, comprising two or more nucleotides of claim 41, wherein each reversible terminator of claim 41 associated with each base B is individually attached to a different fluorescent label such that each base B is detectably distinguishable from any other different base B.
43. The compound according to claim 22, wherein R is chlorophenyl that is optionally substituted.
44. The compound according to claim 22, wherein R is selected from the group consisting of methyl, ethyl, propyl, butyl, pentyl and hexyl.
45. The compound according to claim 19, wherein R is chlorophenyl.
46. The compound according to claim 45, wherein at least one linker group L has the structure depicted in Scheme I:

Scheme I

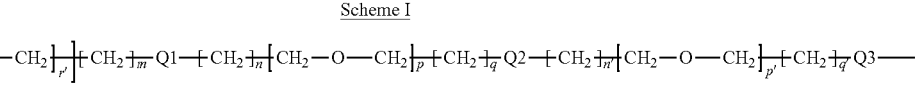

wherein:
m is an integer from 0 to 9,
r and r' are independently either 0 or 1
n and n' are independently either 1 or 2,
p and p' are independently integers from 0 to 18,
q and q' are independently either 1 or 2,
Φ is a cyclic alkane or alkene, an aromatic, heterocyclic or fused ring structure,
Q1-Q3 are independently optional connecting groups, and
the linker group is bound to a nucleotide through the * end.

47. The compound according to claim 46, wherein the at least one linker group is selected from one or more of the group consisting of:

\*—(CH$_2$)$_6$—NHC(O)(CH$_2$)$_n$—NHC(O)—,

\*—CH$_2$(CH$_2$OCH$_2$)$_3$CH$_2$—NHC(O)—(CH$_2$)$_n$—NHC(O)—,

\*—CH$_2$CH(CH$_2$CH$_2$OH)(OCH$_2$CH$_2$)$_m$—NHC(O)—(CH$_2$)$_n$—NHC(O)—,

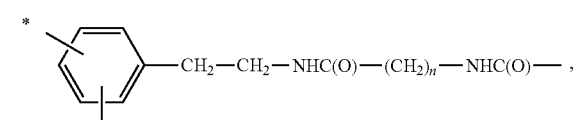

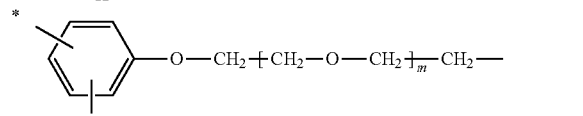

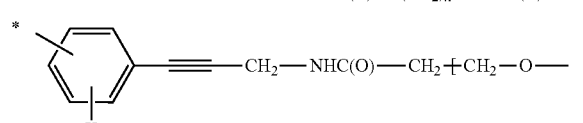

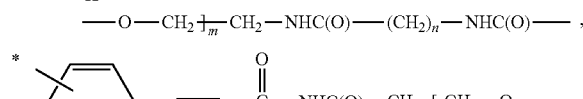

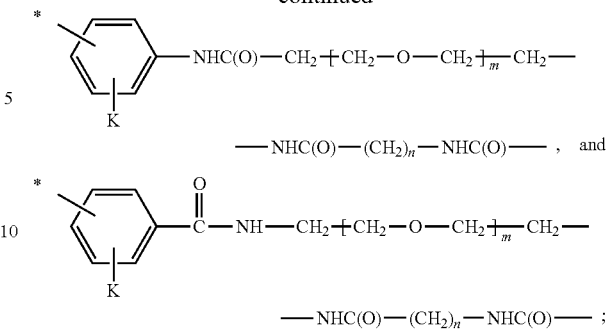

wherein:
K is an optional substituent or functional group,
n is an integer from 2 to 10,
m is an integer from 0 to 18, and
the linker group is bound to a nucleotide through the * end.

48. The compound according to claim 46, wherein Q1-Q3 are independently one or more of the following:

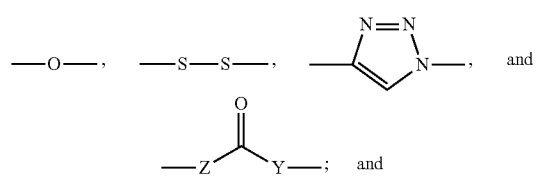

wherein Z and Y are independently optional bridging moieties selected from the group consisting of: O, S, NH, CH$_2$, —CH=CH—, and

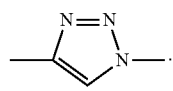

49. The compound according to claim 47, wherein K is a halogen.

50. The compound according to claim 45, wherein D1 and/or D2 are fluorescent detectable labels.

51. The compound according to claim 45, wherein D1 and D2 are acceptor-donor FRET pair labels.

\* \* \* \* \*

```
                        SEQUENCE LISTING

<160> NUMBER OF SEQ ID NOS: 2

<210> SEQ ID NO 1
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 1
ctgaacggta gcatcttgac gagatcggaa gagcgtcgtg tagggaaaga gtgtttcag         59

<210> SEQ ID NO 2
<211> LENGTH: 33
<212> TYPE: DNA
<213> ORGANISM: Artificial Sequence
<220> FEATURE:
<223> OTHER INFORMATION: Synthetic primer

<400> SEQUENCE: 2
acactctttc cctacacgac gctcttccga tct                                      33
```